US007888050B2

(12) United States Patent
Reagan et al.

(10) Patent No.: US 7,888,050 B2
(45) Date of Patent: Feb. 15, 2011

(54) METHOD FOR QUANTIFYING PHOSPHOKINASE ACTIVITY ON PROTEINS

(75) Inventors: Kevin Reagan, Agoura Hills, CA (US); Erik Schaefer, Hopkinton, MA (US); Jimin Wang, Newbury Park, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/179,526

(22) Filed: Jul. 24, 2008

(65) Prior Publication Data

US 2009/0104628 A1 Apr. 23, 2009

Related U.S. Application Data

(63) Continuation of application No. 09/948,972, filed on Sep. 7, 2001, now abandoned.

(60) Provisional application No. 60/235,620, filed on Sep. 27, 2000.

(51) Int. Cl.
*G01N 33/53* (2006.01)
*G01N 33/543* (2006.01)

(52) U.S. Cl. .................. 435/7.21; 435/7.1; 436/501; 436/512; 436/518; 436/540

(58) Field of Classification Search .................. None
See application file for complete search history.

(56) References Cited

U.S. PATENT DOCUMENTS

| | | | |
|---|---|---|---|
| 4,444,879 A * | 4/1984 | Foster et al. ................ | 435/7.95 |
| 5,599,681 A | 2/1997 | Epstein et al. | |
| 5,601,985 A | 2/1997 | Trojanowski et al. | |
| 5,733,734 A | 3/1998 | Trojanowski et al. | |
| 5,763,198 A * | 6/1998 | Hirth et al. ................ | 435/7.21 |
| 5,766,863 A | 6/1998 | Godowski et al. | |
| 5,843,779 A | 12/1998 | Vandermeeren et al. | |
| 6,001,580 A | 12/1999 | Tani et al. | |
| 6,066,462 A | 5/2000 | Goueli | |
| 6,309,863 B1 | 10/2001 | Anderson et al. | |
| 6,680,173 B2 | 1/2004 | Vanmechelen et al. | |
| 6,924,361 B1 | 8/2005 | Laudano et al. | |
| 2003/0162230 A1 | 8/2003 | Reagan et al. | |

FOREIGN PATENT DOCUMENTS

| | | |
|---|---|---|
| EP | 0544942 | 6/1993 |
| JP | 51-026833 | 5/1993 |
| JP | 2000-026498 | 1/2000 |
| JP | 2000-034300 | 2/2000 |
| JP | 2002-350438 | 12/2002 |
| WO | WO-94/13795 | 6/1994 |
| WO | WO-95/17429 | 6/1995 |
| WO | WO-96/04309 | 2/1996 |
| WO | WO-99/24473 | 5/1999 |
| WO | WO 99/29894 * | 6/1999 |
| WO | WO-99/29894 | 6/1999 |
| WO | WO-99/42833 | 8/1999 |
| WO | WO-01/11367 | 2/2001 |

OTHER PUBLICATIONS

Patton et al. (Molecular Biology of the Cell, 1993, vol. 4, No. 2, pp. 159-172-Abstract Only).*
Hosoi et al. (Journal of Biochemistry, 1995, 117/4, pp. 741-749).*
Juan et al. (Experimental Cell Research, 239, 104-110, 1998).*
Vanmechelen et al. (Neuroscience Letters, 285, 2000, pp. 49-52) with cover page dated May 26, 2000.*
Patton et al. "Autophosphorylation of type II CaM kinase in hippocampal meurons: . . . " Molecular Biology of the Cell, 1993, vol. 4, No. 2, pp. 159-172.*
Wen et al. "Retinoblastoma protein monoclonal antibodeis with novel characteristics". Journal if Immunological Methods, 169, 1994, 231-240.*
Juan et al. "Phosphorylation of retinoblastoma susceptibility gene protein assayed in individual lymphocytes during their mitogenic stimulation." Experimental Cell Research, 239, 1998, pp. 104-110.*
Hosoi et al. "Evidence for cdk5 as a major activity phosphorylating tau protein in procine brain extract." Journal of Biochemistry, 117, 1995, pp. 741-749.*
081669121.4, "Extended EP Search Report mailed Feb. 12, 2009".
U.S. Appl. No. 09/948,972, "Office Action mailed Jan. 25, 2008", 12.
U.S. Appl. No. 09/948,972, "Office Action mailed May 19, 2003", 7.
U.S. Appl. No. 09/948,972, "Office Action mailed May 19, 2004", 12.
U.S. Appl. No. 09/948,972, "Office Action mailed Jul. 10, 2007", 20.
U.S. Appl. No. 09/948,972, "Office Action mailed on Jan. 9, 2007", 6.
U.S. Appl. No. 09/948,972, "Office Action mailed on Jun. 13, 2006", 17.
U.S. Appl. No. 09/948,972, "Office Action mailed on Nov. 2, 2005", 14.

(Continued)

*Primary Examiner*—Lisa V Cook

(57) ABSTRACT

The invention involves a method for measuring phosphorylation of proteins at specific sites and, as such, is an indicator of the protein kinase activity of enzymes capable of phosphorylating those sites. The method involves the in vitro or in vivo phosphorylation of a target protein at a specific serine, threonine or tyrosine residue, subjecting that protein (non-phosphorylated) to reaction mixture containing all reagents, including phosphokinase which allow the creation of a phosphorylated form of protein. The phosphorylated protein is measured by contacting it with an antibody specific for the phosphorylation site(s). The invention includes antibodies useful in practicing the methods of the invention. The invention particularly relates to all proteins modified by phosphorylation and dephosphorylation as illustrated by Tau, Rb and EGFR proteins and antibodies specific for the site of phosphorylation of the Tau, Rb or EGFR proteins.

21 Claims, 9 Drawing Sheets

OTHER PUBLICATIONS

U.S. Appl. No. 09/948,972, "Response to Jan. 9, 2007 Office Action filed on Mar. 9, 2007", 10.
U.S. Appl. No. 09/948,972, "Response to May 19, 2003 Office Action, filed Jun. 16, 2003", 4.
U.S. Appl. No. 09/948,972, "Response to May 19, 2004 Office Action filed on Aug. 9, 2004", 18.
U.S. Appl. No. 09/948,972, "Response to Jun. 13, 2006 Office Action filed on Dec. 13, 2006", 18.
U.S. Appl. No. 09/948,972, "Response to Jul. 10, 2007 Office Action filed on Jan. 10, 2008", 25.
U.S. Appl. No. 09/948,972, "Response to Aug. 26, 2003 Office Action", Filed on Dec. 24, 2003.
U.S. Appl. No. 09/948,972, "Response to Nov. 2, 2005 Office Action filed on Jan. 3, 2006", 26.
U.S. Appl. No. 09/948,972, "Office Action mailed Aug. 26, 2003".
Arimura, N. et al., "Phosphorylation of collapsin response mediator protein-2 by Rho-Kinase", Journal of Biological Chemistry vol. 275, No. 31 Aug. 4 2000, 23973-23980.
Bangalore, et al., "Antiserum Raised against a Synthetic Phosphotyrosine-Containing Peptide Selectively Recognizes p185neu/erbB-2 and the Epidermal Growth Factor Receptor", Proceedings of the National Academy of Sciences (PNAS) vol. 89, 1992, 11637-11641.
Biomol International, Inc "Catalog No. SA-307: Anti-phospho-EGFR(pY1173)", www.biomol.com Product Data Biomol, Online Mar. 15, 1997, 1.
Cheng, Xiaodong et al., "Phosphorylation and activation of cAMP-dependent protein kinase by phosphoinositide-dependent protein kinase", Proceedings of the National Academy of Sciences (PNAS) vol. 95, No. 17, Aug. 1998,9849-9854.
Epstein, Richard J. et al., "Synthetic Phosphopeptide Immunogens Yield Activation-Specific Antibodies to the c-erb-2 Receptor", Proceedings of the National Academy of Sciences (PNAS) vol. 89, No. 21, Nov. 1992, 10435-10439.
Forrer, P. et al., "Enzyme-Linked Immunosorbent Assay for Measurement of JNK, ERK, and P38 Kinase Activities", Biological Chemistry vol. 379(1), 1998, 1101-1111.
Gatti, Andrea et al., "Phosphorylation of Human P53 on Thr-55", Biochemistry vol. 39, No. 32, Jul. 21, 2000, 9837-9842.
Herrmann, Martina et al., "ELISA-Quantitation of Phosphorylated Tau Protein in the Alzheimer's Disease Brain", Eur Neurol vol. 42, 1999, 205-210.
Hosoi, Tomoko et al., "Evidence for cdk5 as a Major Activity Phosphorylating Tau Protein in Procine Brain Extract", Journal of Biochemistry 117, 1995, 741-749.
Hulstaert, F. et al., "Improved Discrimination of AD patients using beta-amyloid (1-42) and tau levels in CSF", Neurology vol. 52, 1999, 1555-1562.
Icely, P. L. et al., "TIK, a Novel Serine/Theronine Kinase, is recognized by Antibodies directed Against Phosphotyrosine", Journal of Biological Chemistry vol. 266, No. 24, 1991, 16073-16077.
Ishiguro, Koichi et al., "Phosphorylated tau in human cerebrospinal fluid is a diagnostic marker for alzheimer's disease", Neuroscience Letters, vol. 270, 1999, 91-94.
Jicha, Gregory et al., "Sequence Requirements for Formation of Conformational Variants of Tau Similar to Those Found in Alzheimer's Disease", Journal of neuroscience Research,vol. 55, 1999, 713-723.
Juan, et al., "Phosphorylation of Retinoblastoma Susceptibility Gene Protein Assayed in Individual Lymphocytes during their Mitogenic Stimulation", Experimental Cell Research, 239 1998, 104-110.
Kiroycheva, M. et al., "Mitogen-activated Protein Kinase Phosphorylation in Kidneys of Beta (s) Sickle Cell Mice", Journal of the American Society of Nephrology vol. 11, No. 6, 2000, 1026-1032.
Knudsen, E. S. et al., "Differential Regulation of Retinoblastoma Protein Function by Specific Cdk Phosphorylation Sites", The Journal of Biological chemistry 271 (14), 1996, 8313-8320.
Mahoney, C. W. et al., "High-throughput nonradioisotopic detection of picomole levels of phosphothreonine and phosphoserine containing peptides via biotinylation and enzyme linked immunosorbent Assay", Analytical Biochemistry vol. 268(2) Mar. 15, 1999, 371-376.
Mehta, PD et al., "Increased levels of tau-like protein in patients with Down syndrome", Neuroscience Letters vol. 275, No. 3, Nov. 19, 1999, 159-162.
Mudher, AK et al., "Induction of Hyperphosphorylated tau in living slices of rat hippocampal formation and subsequent detection using an ELISA", J. Neurosci Methods,88(1), Apr. 1, 1999, 15-25.
Palmer, H. et al., "Age-Dependent Decline in Mitogenic Stimulation of Hepatocytes" J. Biol. Chem vol. 274, No. 16, 1999, 11424-30.
Patton, Bruce L. et al., "Autophosphorylation of type II CaM kinase in hippocampal neurons", Molecular Biology of the Cell vol. 4, No. 2, Feb. 1, 1993, 159-172.
Rokka, A. et al., "Dephosphorylation of Photosystem II Reaction Center Proteins in Plant Photosynthetic Membranes as an Immmediate Response to Abrupt Elevation of Temperature", Plant Physiology vol. 123, No. 4 1525-1535, Aug. 2000.
Sorkin, Alexander et al., "Multiple Autophosphorylation Sites of the Epidermal Growth Factor Receptor are essential for Receptor Kinase Activity and Internalization", The Journal of Biological Chemistry vol. 267, No. 12, Apr. 25, 1992, 8672-8678.
Tapiola, T. et al., "Three-year follow-up of cerebrospinal fluid tau, beta-amyloid 42 and 40 concentrations in Alzheimer's disease", Neurosci Lett. 280(2) /2000, 119-122.
Thomas, N. S. et al., "The Phosphorylation State of the Retinoblastoma (RB) Protein in G0/G1 is Dependent on Growth Status", Oncogene vol. 6, No. 2 1991, 317-322.
Vanmechelen, E et al., "Quantification of tau phosphorylated at threonine 181 in human cerebrospinal fluid: a sandwich ELISA with a synthetic phosphopeptide for standardization", Neuroscience Letters vol. 285, No. 1 May 26, 2000, 49-52.
Wen, Shu F. et al., "Retinoblastoma Protein Monoclonal Antibodies with Novel Characteristics", Journal of Immunological Methods vol. 169, No. 2 Mar. 10, 1994, 231-240.
WO 02/027017, "International Search Report", Oct. 16, 2002, 1-8.
Zheng-Fischhoefer, Qingyi et al., "Sequential Phosphorylation of Tau by Glycogen Synthase Kinase-3beta and Protein kinase A at Thr 212 and Ser214 epitope of the antibody AT 100 and requires a Paired-Helical-Filament-Like Conformation", European Journal of Biochemistry vol. 252, No. 3 1998, 542-552.

\* cited by examiner

PEPTIDE COMPETITION FOR ANTI-Rb [pT821]

METHOD FOR QUANTIFYING PHOSPHOKINASE ACTIVITY ON PROTEINS

CROSS-REFERENCE TO RELATED APPLICATIONS

The present application is a Continuation of U.S. patent application Ser. No. 09/948,972, filed Sep. 7, 2001 now abandoned, which claims the benefit of U.S. Provisional 60/235,620, filed Sep. 27, 2000, the contents of which are entirely incorporated herein by reference.

SEQUENCE LISTING

Incorporated herein by reference is a text file containing an Amended Sequence Listing, file name, 547_1_CON_SEQLIST.TEXT, created on Dec. 22, 2008, file size of 956 KB.

FIELD OF THE INVENTION

This invention relates to assays and reagents for measuring protein kinase activity in vitro.

BACKGROUND OF THE ART

Drug development efforts involve a continuum of activities initiated by target selection of a molecule. Since all drugs work at the level of the cell, those targets are usually proteins that somehow are involved in cellular communication pathways. Signal transduction pathways are key to normal cell function. Aberrations in the expression of intracellular molecules and coordinated interactions of signal transduction pathways are associated with a variety of diseases and, thus, are the focus of drug, discovery efforts. Phosphorylation of proteins in signal transduction pathways is one of the key covalent modifications that occur in multicellular organisms. The enzymes that carry out this modification are the protein kinases, which catalyze the transfer of the phosphate from ATP to tyrosine, serine or threonine residues on protein substrates. Phosphorylation of these amino acid residues can alter the function and/or location of the protein within the cell. This change can involve changes in the enzymatic activity of the affected protein and/or create binding sites for the recruitment of other signaling proteins. Because protein kinases are critical components of many cellular signaling pathways, their catalytic activity is often tightly regulated. Abnormalities in protein kinase activity result in different patterns of phosphorylation that can dramatically alter cell function. Indeed, many drug discovery efforts involve the identification of therapeutic agents that selectively suppress or augment protein kinase activity in order to treat a disease. This invention is designed to provide assays and reagents to monitor protein kinase activity.

The targeted residues for phosphorylation can be contained in a full-length, biologically active molecule of recombinant or natural origin. Most methods currently employed for measuring protein kinase activity use peptide substrates, which include the targeted phosphorylation residue. This art is taught in U.S. Pat. No. 6,066,462 (Quantitation of individual protein kinase activity) incorporated herein by reference. This method differs from the present invention in that the peptide substrate does not contain all possible phosphorylation sites that can be acted on by kinases and thus may not truly reflect activity on a natural protein. The invention described herein can be used with whole molecule or fragments, of natural or recombinant origin. Also, the delineation of activity at different phosphorylation sites requires in the invention, a different PSSA for detection as opposed to a different peptide in U.S. Pat. No. 6,066,462.

Another method for detection of kinase activity involves use of a generic antibody that binds to all phospho-tyrosine residues. This method is described in U.S. Pat. No. 5,766,863 (Kinase receptor activation assay) incorporated herein by reference. This method suffers from an inability to discriminate among phosphorylated tyrosine residues on a molecule. This method does not address detection of phospho-serine or phosphothreonine events since the anti-phospho-tyrosine antibody does not detect such phosphorylated residues. In contrast, the method described herein uses antibodies, which bind to the sequence specific residues surrounding the phosphorylated amino acid plus the phospho-residue itself. The reagents used in this invention are capable of detecting phosphorylated threonine, serine or tyrosine molecules.

The current invention and related methods are applicable to a wide range of signal transduction proteins (see Table I for a partial list). Three examples are illustrated below using important molecular targets of current interest in basic research and disease-oriented pharmaceutical study.

Currently, neurobiologists are focusing efforts on the proteins in the brain that can be associated with disease. One such protein is called Tau, a neuronal microtubule associated protein found predominantly in axons. The function of Tau is to promote tubulin polymerization and stabilize microtubules, but it also serves to link certain signaling pathways to the cytoskeleton. Tau phosphorylation regulates both normal and pathological functions of this protein. Tau, in its hyper-phosphorylated form, is the major component of paired helical filaments (PHF), the building block of neurofibrillary lesions that are often found in the brains of individuals with Alzheimer's disease (AD). Hyperphosphorylation impairs the microtubule binding function of Tau, resulting in the destabilization of microtubules in AD brains, ultimately leading to neuronal degeneration. Hyperphosphorylated Tau is also found in a range of other central nervous system disorders. Numerous serine/threonine kinases, including GSK-33, PKA, PKC, CDK5, MARK, INK, p38MAPK and casein kinase II, can phosphorylate Tau.

Detection of in vitro kinase activity is critical for screening compounds that may be able to inhibit this activity and therefore could be useful in ameliorating various neurodegenerative diseases where Tau phosphorylation is abnormally high. Current efforts exist to identify drugs that might suppress kinase activity towards the Tau protein; however, these methods suffer from poor sensitivity and low specificity. Phosphorylation at individual Serine or Threonine residues within the Tau protein has been shown to correlate with disease. This invention overcomes both of these deficiencies in the described 'art'.

U.S. Pat. No. 5,601,985 relates to methods of detecting abnormally phosphory, lated Tau Protein; U.S. Pat. No. 5,843,779 relates to monoclonal antibodies directed against the microtubule-associated protein, Tau, and hybridomas secreting these antibodies; U.S. Pat. No. 5,733,734 relates to methods of screening for Alzheimer's disease or disease associated with the accumulation of paired helical filaments and U.S. Pat. No. 6,066,462 relates to quantitation of individual protein kinase activity. These patents are incorporated herein by reference.

In addition to the detection of Tau phosphorylation in AD, other models exist to show the general applicability of the currently described format for monitoring protein kinase activity. For the purposes of illustration, we have also designed assays around the intranuclear Retinoblastoma (Rb)

protein important in cell cycle regulation and a cell surface receptor molecule (EGFR), which are both described in detail below.

Retinoblastoma protein (Rb), the tumor suppressor product of the retinoblastoma susceptibility gene, is a 110 kDa protein which plays an important role in regulating cell growth and differentiation. Loss of its function leads to uncontrolled cell growth and tumor development. Mutational inactivation of the Rb gene is found in all retinoblastomas and in a variety of other human malignancies including cancers of breast, lung, colon, prostate, osteosarcomas, soft tissue sarcomas, and leukemia. Central to the role of the Rb protein as a tumor suppressor is the ability of Rb to suppress inappropriate proliferation by arresting cells in the GI phase of the cell cycle. Rb protein exerts its growth suppressive function by binding to transcription factors including E2F-1, PU.1, ATF-2, UBF, Elf-1, and c-Abl. The binding of Rb protein is governed by its phosphorylation state. Hypo- or under-phosphorylated forms of Rb bind and sequester transcription factors, most notably those of the E2F/DP family, inhibiting the transcription of genes required to traverse the 01 to S phase boundary of the cell cycle. This cell cycle inhibitory function is abrogated when Rb undergoes phosphorylation catalyzed by specific complexes of cyclins and cyclin-dependent protein kinases (cdks).

Rb contains at least 16 consensus serine/threonine phosphorylation sites for cdks, although the significance of all these sites is still unclear. It has been demonstrated that phosphorylation of threonine 821 on Rh is catalyzed by cdk2/complex such as Cyclin E/cdk2 and Cyclin A/cdk2. The phosphorylation of threonine 821 disrupts the interaction of Rb with the proteins containing the sequence LXCXE, where L=leucine, C=cysteinc, E=glutamic acid, and X=any amino acid residue. The dephosphorylation of Rb protein returns Rb to its active, growth suppressive state. Removal of phosphates on Rb appears to be carried out by a multimeric complex of protein phosphatase type 1 (PP I) and noncatalytic regulatory subunits at the completion of mitosis. The quantitation of Rb phosphorylated at specific amino acid residues gives important information regarding the activity of kinases as well as the functional state of the Rb protein itself. For the purposes of illustration, we designed an assay to quantitate the amount of Rb protein that is specifically phosphorylated at threonine 821 using an ELISA format. This assay does not recognize Rb phosphorylated at sites other than [$pT^{821}$] or when it is in the non-phosphorylated form. Samples can be controlled for Rb content by parallel measurement of total Rb protein.

WO 01/11367 (Assay of the phosphorylation activity of cyclin/CDK complex on retinoblastoma (RB) protein for identifying compounds which modify this activity) describes a method for detecting kinase activity by ELISA using a synthetic peptide and a monoclonal antibody that recognizes the phosphorylated form of the peptide. The basis of this method is the coating of a solid phase with a synthetic peptide containing the consensus sequence of a region upon which a kinase acts. The peptide is allowed to come in contact with a kinase that allows a specific residue on that peptide to become phosphorylated. The activity of the kinase then is estimated by the binding of the generic monoclonal antibody to the target phosphopeptide. Our invention differs from WO 01/11367 in that it uses a natural protein as the substrate for kinase activity. This feature is superior to the use of peptides since all naturally occurring phosphorylation sites would be present and the protein would be presented in its normal conformation. The use of a single monoclonal antibody recognizing phosphoserine (clone 2B9) also does not allow any discrimination of the many phosphorylation sites that naturally occur on Rb protein. Our use of specific PSSAs allows that distinction as well as the detection of phosphothreonine and phosphotyrosine residues allowing a profile of Rb phosphorylation sites to be constructed.

As a third example of the utility of this approach, a cell surface receptor was studied and a kinase-dependent ELISA designed. The Epidermal growth factor receptor (EGFR) belongs to the family of receptor tyrosine kinases (RTKs), which regulate cell growth, survival, proliferation and differentiation. EGFR is expressed at full length as a 170 kDa type I transmembrane glycoprotein which consists of an extracellular ligandbinding domain, a single hydrophobic transmembrane region, and an intracellular domain that exhibits tyrosine enzymatic activity and which is involved in signal transduction. Several deletions in the extra- and intracellular domain of the EGFR have been found in a number of tumors. For example, EGFRvill is a 145 kDa protein with a deletion of exons 2-7 in EGFR mRNA. A 100 kDa truncated EGFR without the cytoplasmic domain is observed in the culture supernatant from A431 cells, a human epidermal carcinoma cell line.

EGFR is activated by binding of a number of ligands such as EGF, transforming growth factor a (TGFα), amphiregulin, betacellulin, heparin binding EGF-like growth factor (HB-EGF) and epiregulin. The binding causes EGFR homo- and heterodimerization and autophosphorylation of multiple tyrosine residues in the cytoplasmic domain, which involves rapid activation of its intrinsic tyrosine kinase activity. Phosphorylation of tyrosine residues in the COOH-terminal tail of the EGFR. serve as binding sites for cytosolic signaling proteins containing Src homology 2 (SH2) domains. Several sites of in vivo phosphorylation have been identified in the EGFR including $Tyr^{845}$, $Tyr^{992}$, $Tyr^{1068}$, $Tyr^{1086}$, and $Tyr^{1173}$. These sites bind and activate a variety of downstream signaling proteins that contain SH2 domains, including growth factor receptor-binding protein 2 (Grb2), Src homology and collagen domain protein (She) and phospholipase C-γ (PLCγ). The binding of these or other signaling proteins to the receptor and/or their phosphorylation results in transmission of subsequent signaling events that culminate in DNA synthesis and cell division.

Elevated expression and/or amplification of the EGFR have been found in breast, bladder, glioma, colon, lung, squamous cell, head and neck, ovarian, and pancreatic cancers. Selective compounds have been developed that target either the extracellular ligand-binding domain of EGFR or the intracellular tyrosine kinase region, resulting in interference with the signaling pathways that modulate mitogenic and other cancer-promoting responses. These potential anticancer agents include a number of small molecule, tyrosine kinase inhibitors.

SUMMARY OF THE INVENTION

The invention describes assays and reagents for quantitating phosphorylation of proteins. The method involves subjecting a protein to a protein kinase that will phosphorylate the protein and binding this specific phosphorylated form of the protein with an antibody specific for the amino acid sequence containing the phosphorylated site and detecting the primary antibody bound to the phosphorylated site. The invention includes antibodies useful in practicing the methods of the invention. The invention particularly relates to phosphorylation of Tau, Rb, and EGFR proteins and antibodies specific for the sites of phosphorylation within the Tau, Rb, and EGFR proteins. However, the invention can be applied to all proteins and antibodies that recognize specific phosphorylation sites on these proteins (see Table I).

In each example system, the targeted protein (Tau, Rb or EGFR) is phosphorylated in vitro or in vivo and the specific phosphorylation event is detected using a highly selective phosphorylation site-specific antibody (PSSA). The appearance or disappearance of the targeted phosphorylation event can be quantified as a percentage of total protein that may be phosphorylated at each site.

The highly specific nature of the PSSAs allows parallel independent measurement of multiple phosphorylation sites on one protein. Moreover, different kinases can be measured simultaneously by using different PSSAs that selectively target different sites in the protein, thereby providing an avenue for generating phosphorylation site profiles. In contrast to existing methods that quantitate phosphorylated proteins as a diagnostic or prognostic indication of disease, this invention measures protein kinase enzymatic activity that results in the phosphorylation of proteins at a specific sites. This method is also amenable to large-scale 'High Throughput Screening' formats currently being used by pharmaceutical and biotech companies to discover new drugs that block specific phosphorylation events.

BRIEF DESCRIPTION OF THE DRAWINGS

FIG. 3A shows results of assay using phosphorylated Tau. FIG. 3B shows results of assay for non-phosphorylated Tau.

DETAILED DESCRIPTION OF THE INVENTION

Tau System: The Tau protein system demonstrates the utility of this invention on a protein that is found both intracellularly and extracellularly in normal and pathological conditions. The Tau protein has multiple phosphorylation sites acted upon by multiple protein kinases. Phosphoserine and phosphotyrosine residues exist. Both mono-phospho and dual-phosphoresidues are distinguishable in this model system.

Tau Recombinant Protein: Full length Tau-441 protein is purified recombinant protein derived through cloning of human Tau cDNA and expressed in *E. coli*. The protein is purified via standard methods. This protein is commercially available from multiple vendors.

Tau $pS^{199}$ PSSA: Rabbits were immunized with a chemically synthesized and KLH conjugated phosphopeptide corresponding to the region of the longest isoform of the Tan protein that includes serine 199. The chemically synthesized phosphopeptides (RSGYS (pS) PGSPG) is sequence ID #I. The Tau $pS^{199}$ PSSA was purified from rabbit serum by sequential epitope-specific chromatography. The antibody was negatively preadsorbed using a non-phosphopeptide corresponding to the site of phosphorylation to remove antibody that is reactive with non-phosphorylated Tan. The final product was generated by affinity chromatography using the peptide that is phosphorylated at serine 199. This antibody recognizes specifically the Tau protein when phosphorylated on serine 199, as demonstrated by peptide competition analysis in a western blotting assay. Serine 199 is phosphorylated in vitro and in vivo by glycogen synthase kinase-3β (GSK-3β), which is commercially available.

Figure 1:
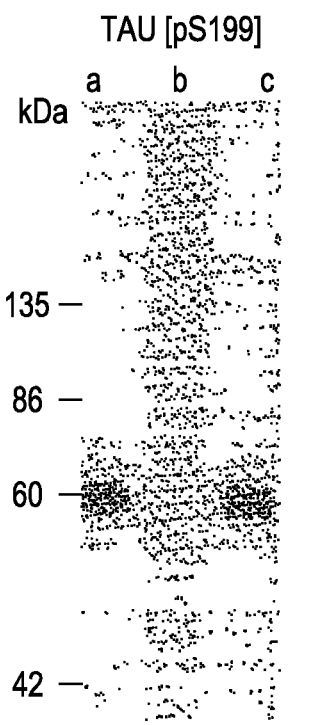
FIG. 1 illustrates specificity of the Anti-phospho Tau [$pS^{199}$] in phosphorylation site-specific antibody (PSSA).

The specificity of the anti-Tau [pS199] PSSA Tau specificity is shown in FIG. 1. Cell extracts from African green monkey kidney (CV-1) cells; stably expressing human four repeat tau and a protein phosphatase inhibitor, were resolved by SDS-PAGE on a 10% Tris-glycine gel. The proteins were transferred to nitrocellulose. Membranes were incubated with 0.50 µg/mL anti-phosphoTau [$pS^{199}$], following prior incubation in the absence (a) or presence of the peptide immunogen (b), or the non-phosphopeptide corresponding to the tau phosphopeptide (c). After washing, membranes were incubated with goat F(ab')$_2$ anti-rabbit IgG alkaline phosphatase and bands were detected using the Tropix Western-Star™ detection method. The data in FIG. 1 show that only the phosphopeptide corresponding to this site blocks the antibody signal, illustrating the specificity of the Anti-Tau [$pS^{199}$] antibody for this phosphorylation site.

Tan [$pS^{241}$] PSSA. The procedures for generating this antibody were similar to those described above for the Tau $pS^{199}$ PSSA. The chemically synthesized phosphopeptide was derived from the region of the longest isoform of Tau protein that includes serine 214 (GSRSRTP(pS)LPTPP) sequence ID#2. This antibody recognizes specifically the Tau protein when phosphorylated on serine 214 as demonstrated by peptide competition analysis in a western blotting assay. Serine 214 is phosphorylated in vitro and in vivo by cAMP-dependent protein kinase (PICA), which is commercially available from Biosource International.

Figure 2:
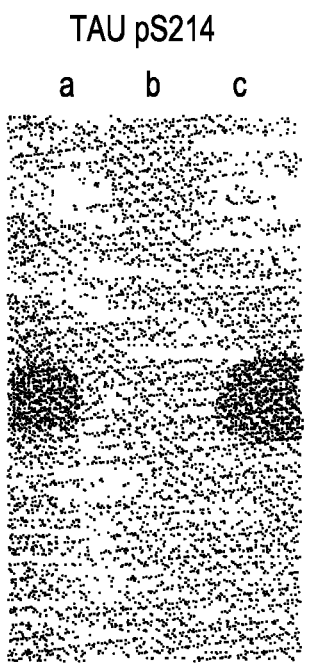
FIG. 2 illustrates Anti-phospho Tau [$pS^{124}$] PSSA specificity.

Tau $pS^{214}$ PSSA specificity is show in FIG. 2. SF-9 cell extracts, expressing human four repeat tau, were resolved by SDS PAGE on a 10% Tris-glycine gel. The proteins were transferred to nitrocellulose. Membranes were incubated with 0.50 ug/mL. anti-phospho tau [pS$^{214}$], following prior incubation in the absence (a) or presence of the peptide immunogen (b), or the non-phosphopeptide corresponding to the tau phosphopeptide (c). After washing, membranes were incubated with goat F(ab')$_2$ anti-rabbit IgG alkaline phosphatase and bands were detected using the Tropix Western-Star™ method. The data in FIG. 2 show that only the phosphopeptide corresponding to this site blocks the antibody signal, illustrating the specificity of the Anti-Tan [pS$^{214}$] antibody for this phosphorylation site. PSSAs to other Tau sites [pS$^{202}$, pS$^{396}$, pT$^{118}$, pS$^{199}$/pS$^{202}$, pS$^{404}$] have been characterized using similar methods.

Pan-Tau Polyclonal Antibody

Rabbits were immunized with the recombinant Tau protein and the resulting antibody was purified from the rabbit serum using a protein-A affinity column. This antibody recognizes multiple antigenic sites on Tau protein. This antibody will bind to both non-phosphorylated and phosphorylated forms of Tau protein.

Tau-5 Monoclonal Antibody (mAb)

The mouse mAb to Tau was raised using purified bovine microtubule-associated proteins (MAPs) as the immunogen. The resulting hybridoma was produced by fusing immunized BALB/c mouse splenocytes and mouse myeloma Sp2/0-Agl4 cells. It shows no cross-reaction with other MAPs or tubulin. it reacts with the non-phosphorylated as well as the phosphorylated forms of Tau and the reactive epitope maps to residues 210-230. This reagent is commercially available from Biosource International.

Total Tau ELISA and Phospho-Tau ELISA

A concentration of 2.5 μg/mL of Tau-5 monoclonal antibody in carbonate buffer, pH 9.4, was incubated at 100 μL/well in microtiter plates at 4° C. overnight. The wells were washed with a PBS/TWEEN-20 solution three times followed by blocking on other sites on the plastic surface with a buffered solution containing unrelated proteins such as BSA for 2 hours at room temperature. GSK-3β phosphorylated Tau, PKA phosphorylated Tau, and nonphosphorylated Tau were added to the wells at various concentrations and incubated for 1 hour at room temperature. After washing 3 times with Washing Buffer, the wells were incubated respectively with Tau pS$^{214}$ PSSA, Tau pS$^{199}$ PSSA or Pan-Tau antibodies at the optimized concentrations (ranging from 0.1 to 1 μg/mL) for 1 hour at room temperature. The plates then were washed three times with Washing Buffer, followed by the addition of an HRP conjugated anti-rabbit IgG secondary antibody at 1:5000 dilution for 1 hour at room temperature. After washing 3 times, 100 μL of Stabilized Chromogen was added to each well and then incubated for 20 minutes at room temperature in the dark. The OD values at 450 nm were measured following the addition of stop solution to each well.

Kinase Reactions

Phosphorylation of Tau using PKA was performed as follows. PICA was purchased from New England Biolabs. Recombinant Tau protein (1 μg) was incubated with various concentrations of PKA enzyme in buffer containing 50 mM Tris-HCl (pH 7.5), 10 mM MgCl$_2$ and 100 A1 ATP for 1 hour at 30° C.

Phosphorylation of Tau Using GSK-3β

GSK-3β was purchased from Upstate Biotechnology Inc. Recombinant Tau protein (1 pg) was incubated with various concentrations of the enzyme in buffer containing 40 mM HEPES (pH 7.2), 5 mM MgCl$_2$, 5 mM EDTA, 100 μM ATP, and 50 μg/mL heparin for 1 hour at 30° C.

Figure 3A:
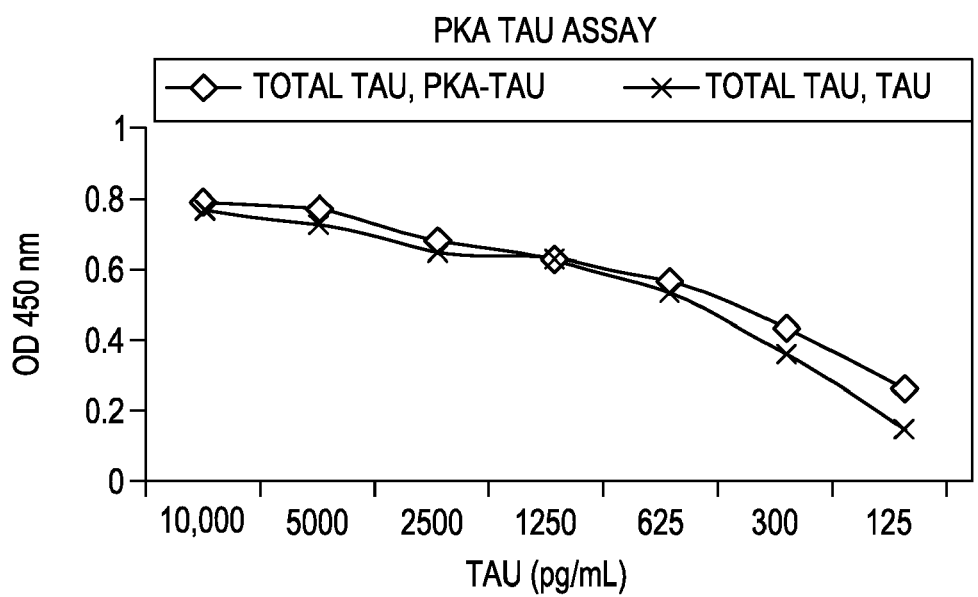
FIG. 3A and 3B illustrate detection of total Tau vs. Tau phosphorylated at the PKA/serine 214 site by ELISA.
Figure 3B:
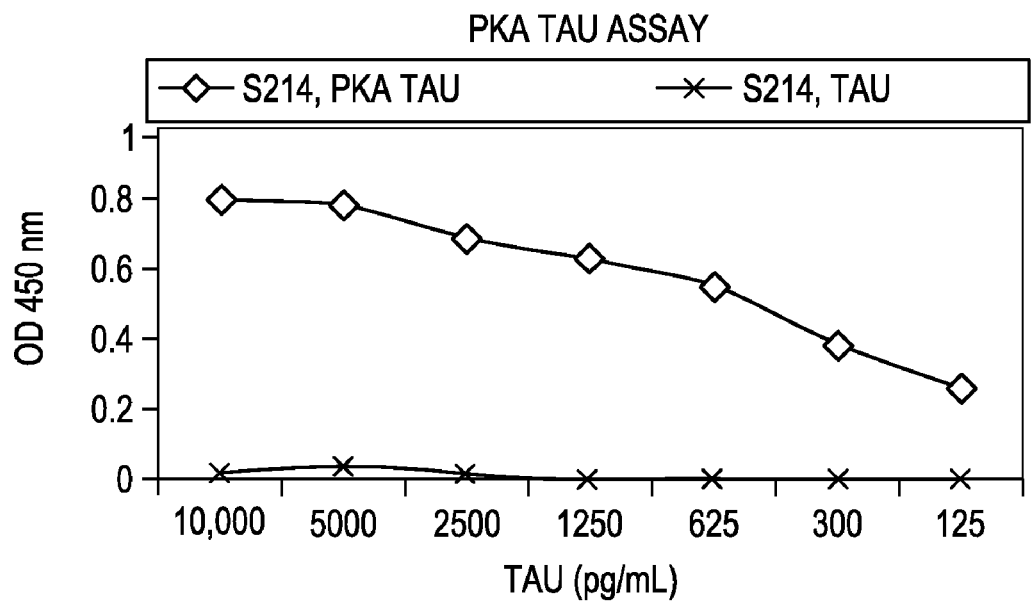

FIGS. 3a and 3b show the assessment of total Tau and selective Tau phosphorylation at the PKA/Ser$^{214}$ site by ELISA. In FIG. 3a, phosphorylated Tau was detected by an ELISA using a PSSA specific for Tau pS$^{214}$ or by a pan-Tau antibody. Both antibodies detected the phosphorylated Tau protein with equal signals. In FIG. 3b, non-phosphorylated Tau was placed into the same assay. As expected, the anti-Tau [pS$^{214}$] antibody failed to detect the Tau protein lacking the phosphate group at serine 214, whereas the pan-Tau antibody did detect the Tau protein.

Figure 4A:
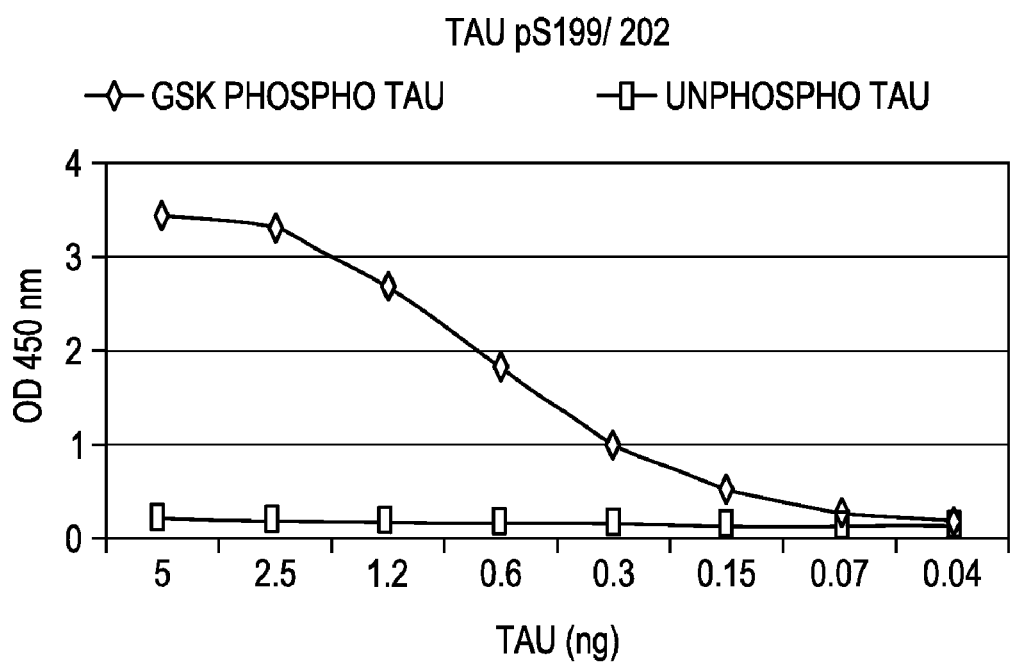
FIG. 4A and B illustrate detection Tau phosphorylated at GSK-3b/serine 199/202 (4A) vs. total Tau (4B) sites by ELISA.
Figure 4B:
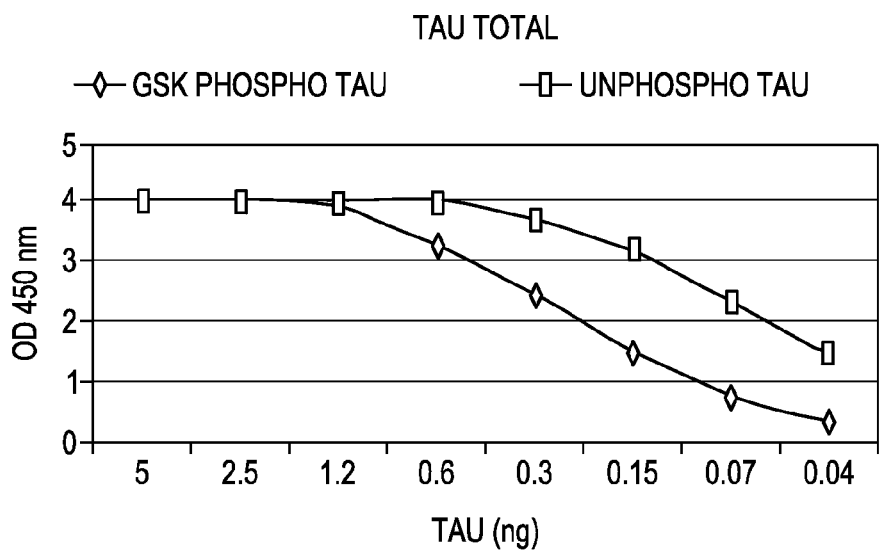
Figure 5:
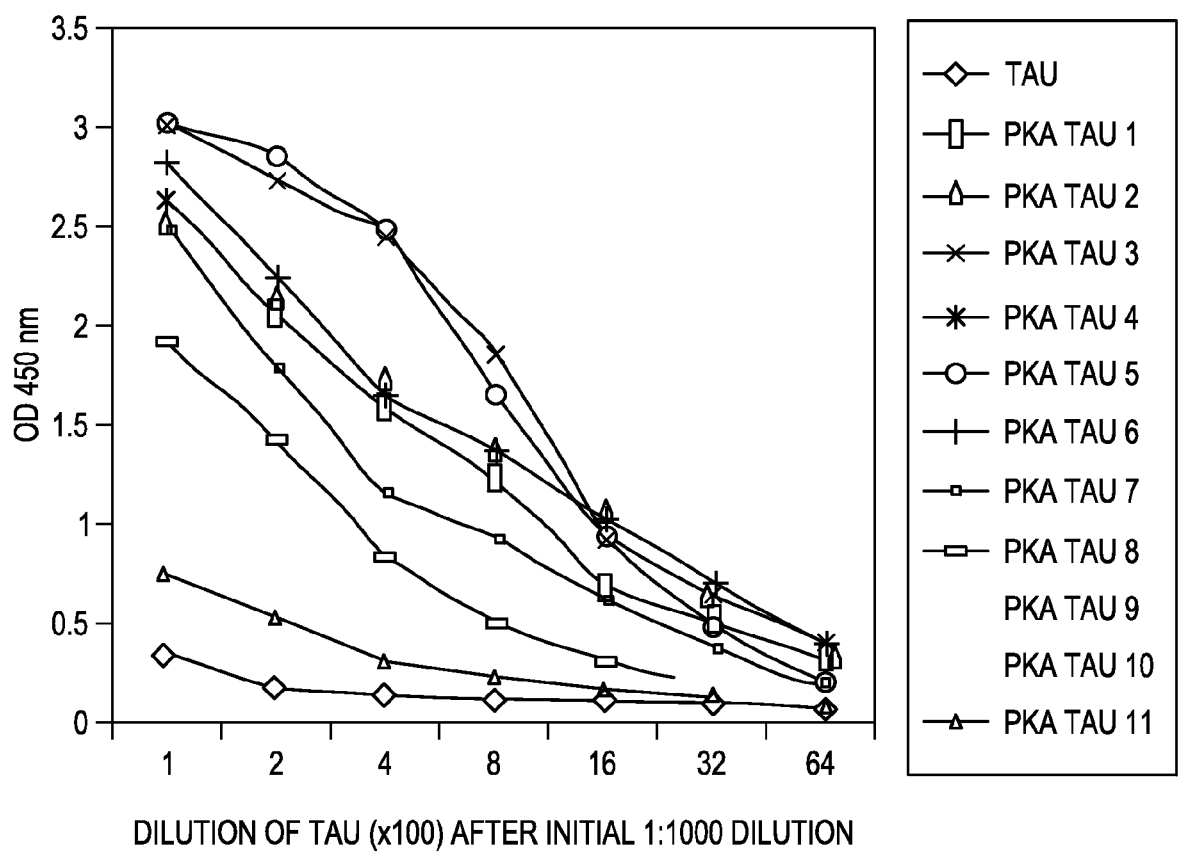
FIG. 5 illustrates a dose-response curve generated in an ELISA using the Tau serine 214 PSSA.

FIGS. 4a and 4b show the assessment of total Tau vs. selective Tau phosphorylation at the GSK-3β/Ser$^{199/202}$ sites by ELISA. FIG. 4a uses either non-phosphorylated Tau or GSK-3β-phosphorylated Tau in the ELISA with the anti-Tau pS$^{199/202}$ antibody. Nonphosphorylated Tau does not react in the ELISA, whereas the phosphorylated Tau shows strong signals. If the pan-Tan antibody is used as the detector, both proteins are readily detected (FIG. 4b). FIG. 5 shows the direct relationship between the amount of phospho-Tau protein detected by ELISA and the quantity of protein kinase activity in the in vitro reaction. Various amounts of PKA enzyme were used to phosphorylate the Tau protein. Starting with the highest concentration of PKA, 5 units, (PICA tau 1), the PICA enzyme was then serially diluted 1:2 as shown, followed by a 1:1000 dilution and then applied to each well of the ELISA. Detection of phosphoTau was performed using the anti-Tau [pS214] (a PKA site). These data indicate that lower amounts of protein kinase in the reaction result in a proportionally lower amount of phosphoprotein produced, as detected in the ELISA. Thus, the ELISA signal provides an indirect, yet quantitative, measure of phosphokinase activity.

Figure 6A:
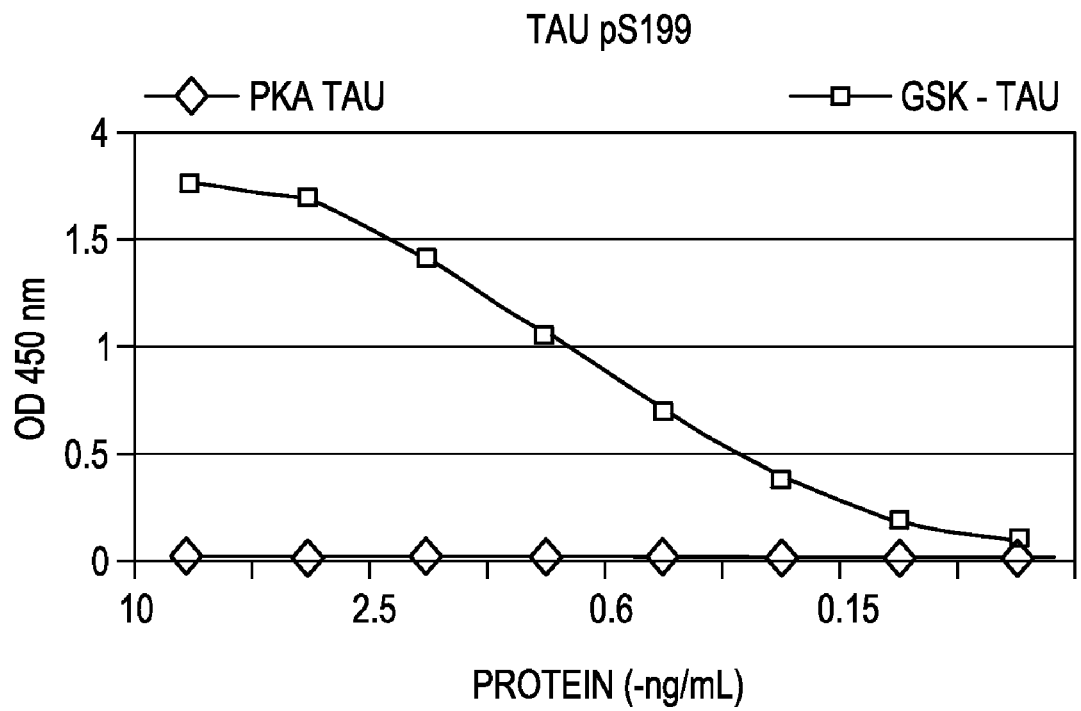
FIG. 6 illustrates the specificity of the Tau PSSAs in an ELISA to detect Tau phosphorylation catalyzed by PKA vs. GSK-3β enzymes.
Figure 6B:
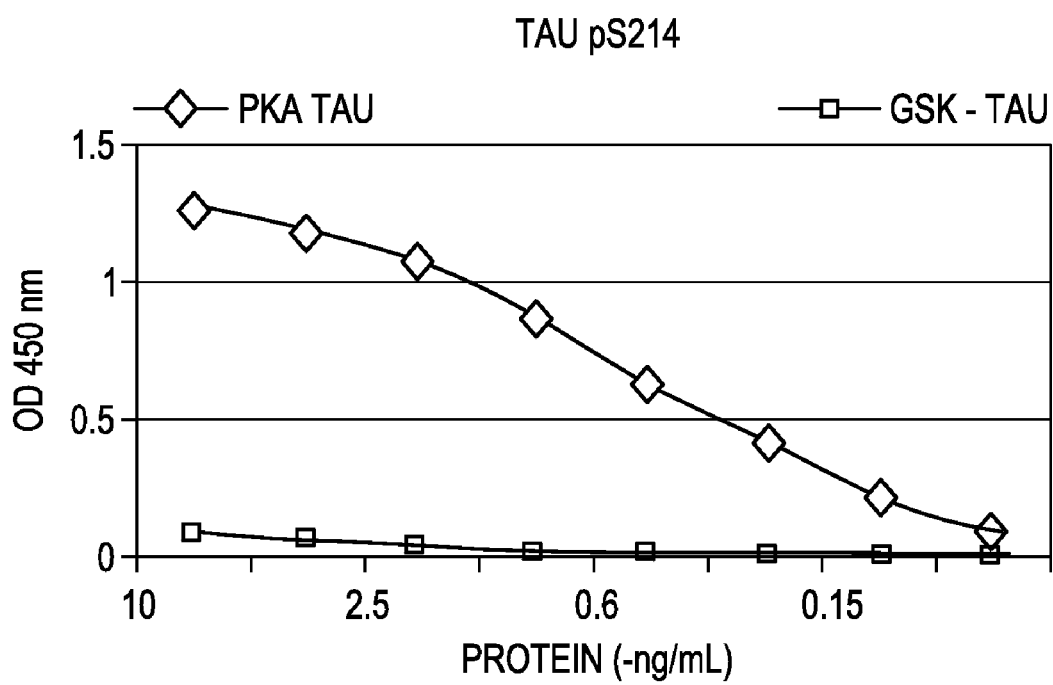

FIGS. 6a and 6b shows the specificity in detecting Tau protein phosphorylation catalyzed by PICA vs. G8100 enzymes using the Tau PSSAs and ELISA. The results demonstrate that the Tau pS$^{214}$ PSSA ELISA only detects Tau when phosphorylated by PICA and the Tau pS$^{199}$ PSSA ELISA only detects Tau when phosphorylated by GSIC3p.

Figure 7:
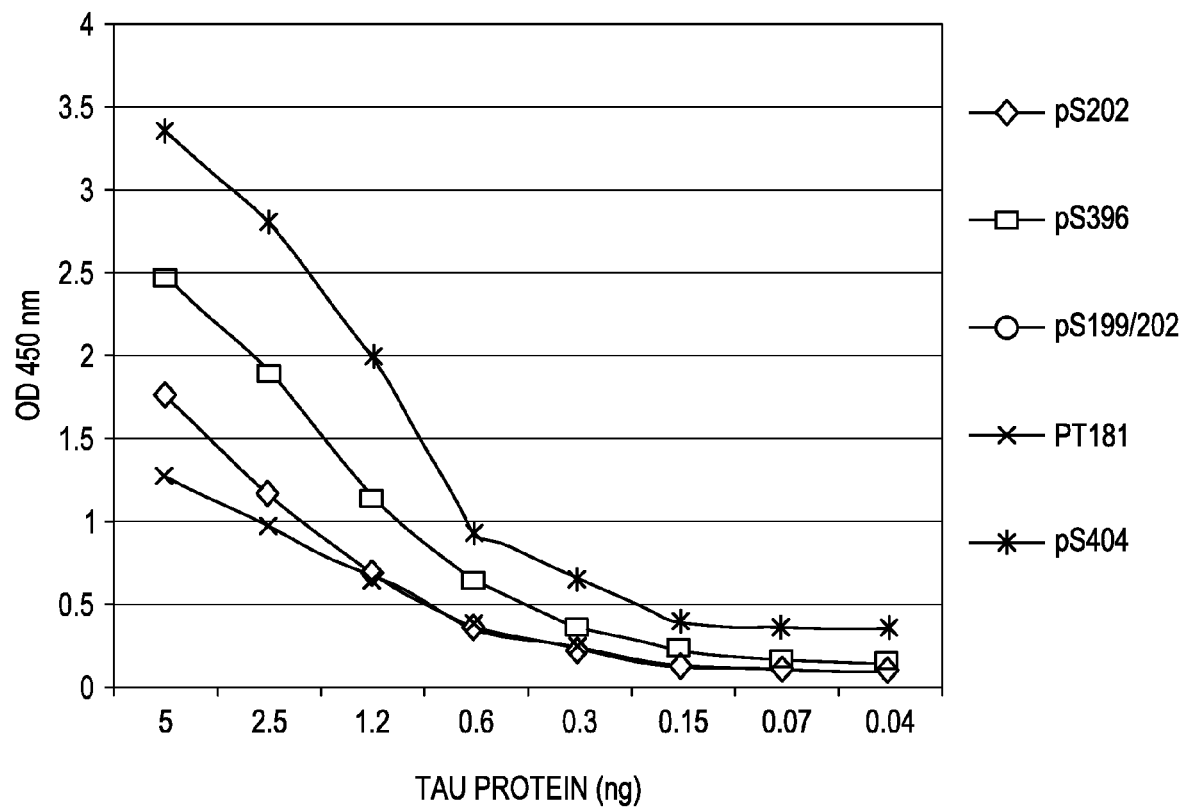
FIG. 7 illustrates that multiple GSK-3β phosphorylation sites on Tau can be detected by ELISA using Tau PSSAs.
Figure 8:
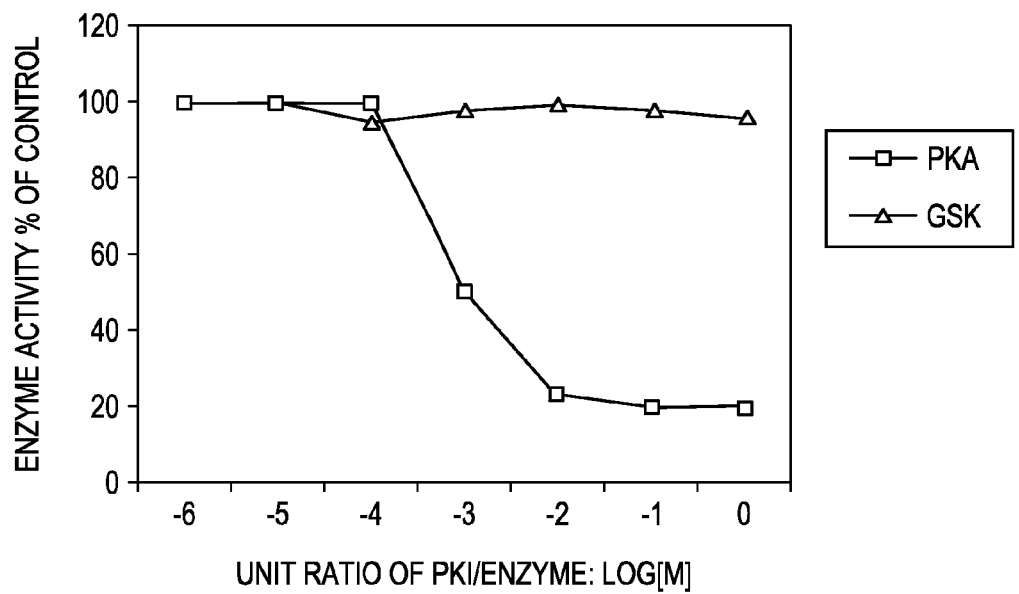
FIG. 8 illustrates that a specific inhibitor of PKA activity selectively inhibits the phosphorylation on serine 214 of Tau but does not interfere with GSK enzyme activity as demonstrated using Tau [$pS^{214}$] and Tau [$pS^{199}$] PSSAs as detected by ELISA.

FIG. 7 shows that the GSK3β enzyme can phosphorylate multiple sites on the Tau protein and PSSAs can independently detect the phosphorylated sites at Tau pT$^{181}$, Tau pS$^{202}$, Tau pS$^{199}$/pS$^{242}$, Tau pS$^{396}$, and Tau pS$^{404}$. This provides evidence that the ELISA is useful in creating a profile of phosphorylation events on the protein subjected to kinase enzyme activity. FIG. 8 shows the specificity of kinase reaction when tested as a profile with two antibodies, one specific for a PKA phosphorylation site (pS$^{214}$) and the other for a GSK site (pS$^{199}$) on Tau protein. A PKA-specific inhibitor, PKI (heat-stable inhibitor of c-AMPdependent protein kinase; New England Biolabs), was mixed at various ratios of inhibitor to enzyme (either PICA or GSK) and the resultant mixture analyzed by ELISA using the Tau PSSAs. The PICA-specific inhibitor altered the kinase activity of the pS$^{214}$ site alone. These data again attest to the specificity of the ELISA and the ability to independently monitor kinase activities on the same protein at different sites using the highly specific PSSAs as the assay detectors. These data also illustrate the capability of selectively screening for drug interference of protein kinase activity using this format.

Antibodies to other tau sites shown in Table II are also representative of the invention. Some of the phosphorylated sites are known to be associated with disease as further indicated in Table II.

TABLE II

| Phospho Site | Disease Linked (Y/N/?) | Notes (NGD = Neurodegenerative disease; FTD = Frontotemporal Dementia) |
|---|---|---|
| T39 | ? | Phosphorylated by Casein kinase II |
| T181, hu | ? | Involved in pretangle process? |
| S184 | Y | Phosphorylated by GSK-3b; disrupts microtubule network |
| S195 | Y | Phosphorylated by GSK-3b; disrupts microtubule network |
| S198 | Y | Phosphorylated by GSK-3b; disrupts microtubule network |
| S199 | Y | Phosphorylated by GSK-3b; linked to hereditary FTD |
| S202 | Y | Microtubule-dependent phosphorylation by CDK 5 and GSK-3b; linked to hereditary NGD |
| T205 | Y | Microtubule-dependent phosphorylation by CDK 5 and GSK-3b |
| T212 | Y | Specific for NGD processes; phosphorylated by GSK-3b and PKA |
| S214 | Y | Specific for NGD processes; may block aggregation; phos'd by PKA |
| T217 | ? | |
| T231 | Y | Involved in pretangle process?; phos'd by GSK-3b and cdc2/CDK1 |
| S235 | ? | Microtubule-independent phosphorylation by GSK-3b |
| S262 | Y | May block aggregation; phosphorylated by CAM K II and GSK-3b; major site in AD brain |
| S320 | ? | |
| S324 | ? | |
| S356 | Y | Involved in pretangle process?; AD pathway; major site in AD brain; phosphorylated by GSK-3b |
| S361 | ? | |
| S396 | N | Phos'd by GSK-3b |
| S400 | ? | Phos'd by GSK-3b |
| T403 | ? | |
| S404 | ? | Involved in pretangle process?; microtubule-independent phosphorylation; phosphorylated by GSK-3b |
| S409 | Y | AD pathway; phosphorylated by PKA |
| S412 | ? | AD pathway |
| S413 | Y | AD pathway; phosphorylated by GSK-3b |
| S416 | ? | Phosphorylated by CAM K II |
| S422 | Y | Linked with several NGD's; phosphorylated by MAPK |

Rb System: This model system describes a large intra-nuclear protein with multiple phosphorylation sites that are acted upon by multiple protein kinases. Both phosphoserine and phosphotyrosine residues are examined, for which both mono-phospho and dual-phosphoresidues are distinguishable in this model system.

Rb protein: Full length Rb protein is purified recombinant protein derived through cloning of human Rb cDNA and expressed in *E. coli*. The protein is purified via standard methods. This protein is commercially available from multiple vendors.

Figure 9:
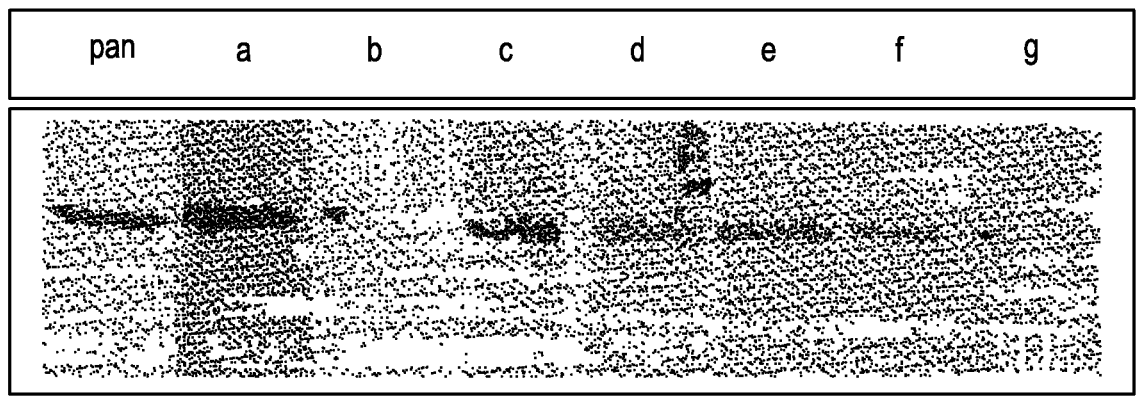
FIG. 9 defines the specificity of the anti-Rb [$pT^{821}$].

Rb [pT$^{821}$] PSSA: The rabbit antiserum was produced against a chemically synthesized phosphopeptide derived from a region of human Rb that contains threonine 821. Antibody was purified from rabbit serum by sequential epitope-specific chromatography. The antibody has been negatively preadsorbed using a non-phosphopeptide corresponding to the site of phosphorylation to remove antibody that is reactive with non-phosphorylated Rb. The final product is generated by affinity chromatography using a Rb-derived peptide that is phosphorylated at threonine 821. FIG. 9 defines the specificity of the anti-Rb [pT$^{821}$]. SDS-PAGE on a 7.5% Tris-glycine gel resolved cell extracts, prepared from MCF-7 cells. The proteins were then transferred to PVDF. Membranes were incubated with 0.5 g/mL antiRB[pT$^{821}$] following prior incubation in the absence (a) or presence of the peptide immunogen (b), the non-phosphopeptide corresponding to the RB phosphopeptide (c), the phosphopeptides corresponding to threonine 356 (d), serine 807/811 (e), serine 249/threonine 252 (f), and serine 751 (g) on phospho-RB. After washing, membranes were incubated with goat F(ab')$_2$ anti-rabbit IgG alkaline phosphatase and bands were detected using the Tropix WesternStar™ method. The data show that only the phosphopeptide corresponding to this site blocks the antibody signal, demonstrating the specificity of the anti-Rb [pT$^{821}$] antibody for this phosphorylated residue.

Total Rb [pan] Detection Antibody: the detection antibody is a monoclonal, clone G3-245, available commercially from BD/Pharmingen (San Diego, Calif.). It recognizes an epitope between amino acids 332-344 of Rb protein. This antibody will bind to both nonphosphorylated and phosphorylated forms of Rb protein.

Rb monoclonal antibody: the capture antibody [linked to the solid phase] is a monoclonal, clone 3C8, available commercially from QED Biosciences (San Diego, Calif.). It reacts with epitope on near the C-terminal end of the Rb protein (aa886-aa905). This antibody will bind to both non-phosphorylated and phosphorylated forms of Rb protein.

Total Rb and Rb [pT$^{821}$] ELISA: A concentration of 1.25 µg/ml, of Rb monoclonal antibody in carbonate buffer, pH 9.4, was incubated at 100 µL/well in microtiter plates at 4° C. overnight. The wells were washed with a PBS/TWEEN-20 solution three times followed by blocking on other sites on the plastic surface with a buffered solution containing unrelated proteins such as BSA for 2 hours at room temperature. Jurkat cell lysate containing phosphorylated Rb or non-phosphorylated recombinant Rb were added to the wells at various concentrations and incubated for 2 hour at room temperature. After three washings with Washing Buffer, the wells were incubated, respectively, with Rb [pT$^{821}$] PSSA and biotinylated Pan-Rb antibodies at the optimized concentrations (ranging from 0.1 to 1 µg/mL) for 1 hour at room temperature. The plates then were washed three times with Washing Buffer, followed by the addition of an HRP conjugated anti-rabbit IgG secondary antibody at 1:5000 dilution or 0.25 µg/mL of streptavidin-HRP for 1 hour at room temperature. After washing, 100 µL of Stabilized Chromogen was added to each well and then incubated for 20 minutes at room temperature in the dark. The OD values at 450 nm were measured following the addition of stop solution to each well.

Figure 10:
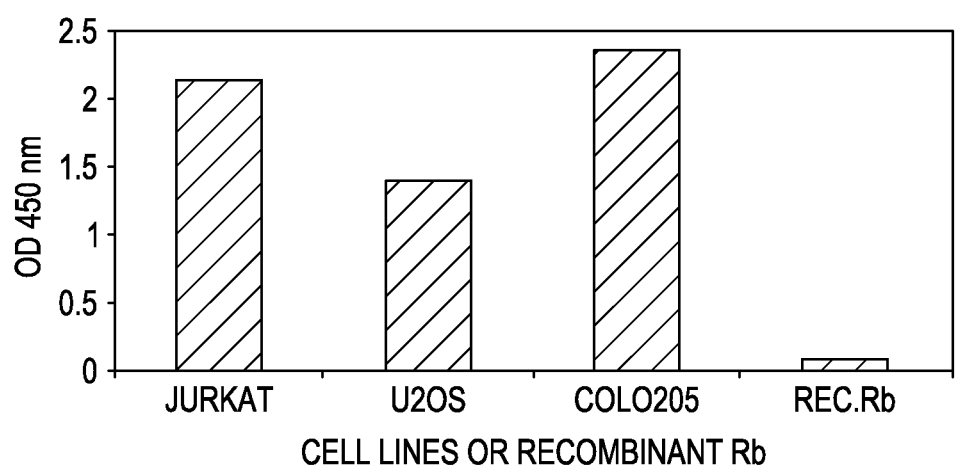
FIG. 10 shows studies to determine the specificity of the Rb [$pT^{821}$] ELISA.
Figure 11:
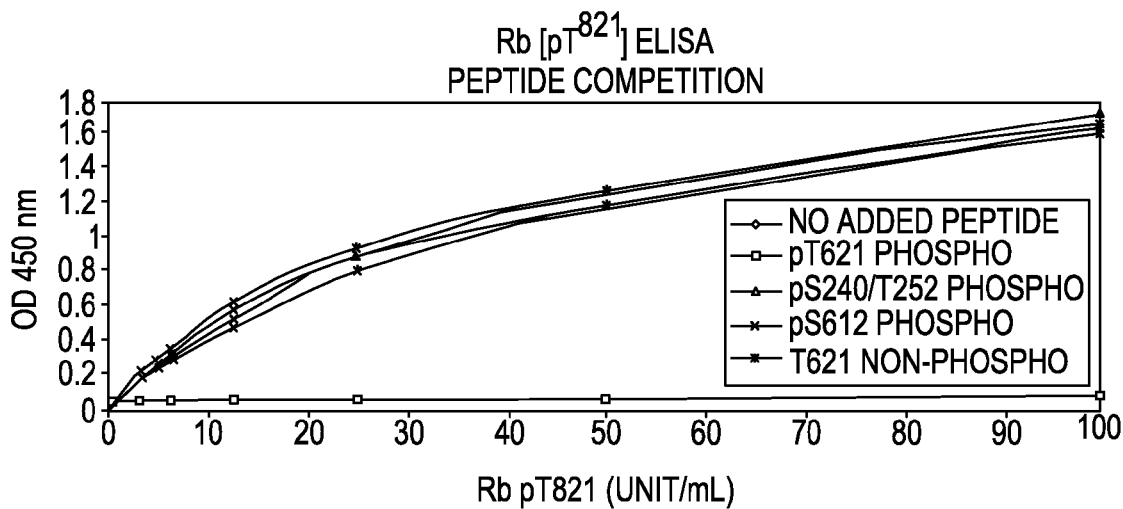
FIG. 11 shows the specificity of the Rb [$pT^{821}$] ELISA for threonine 821 as determined by peptide competition.

FIG. 10 shows studies to determine the specificity of the Rb [pT$^{821}$] ELISA. In the first study, solutions containing Rb protein at a concentration of 20 ng/mL from Jurkat, U2OS, and Colo205 were analyzed with the Rb [pT$^{821}$] ELISA kit, along with a solution containing 20 nglmL purified full length Rb protein expressed in *E. coli* (non-phosphorylated). FIG. 11 shows that the Rb protein isolated from the cell lines was strongly recognized. These data provide evidence that appropriate phosphorylation of the Rb protein is requisite for reactivity in this assay.

In the second study, specificity for threonine 821 was determined by peptide competition. The data presented in FIG. 11 show that only the peptide corresponding to the region surrounding threonine 821, containing the phospho-threonine, could block the ELISA signal.

Figure 12:
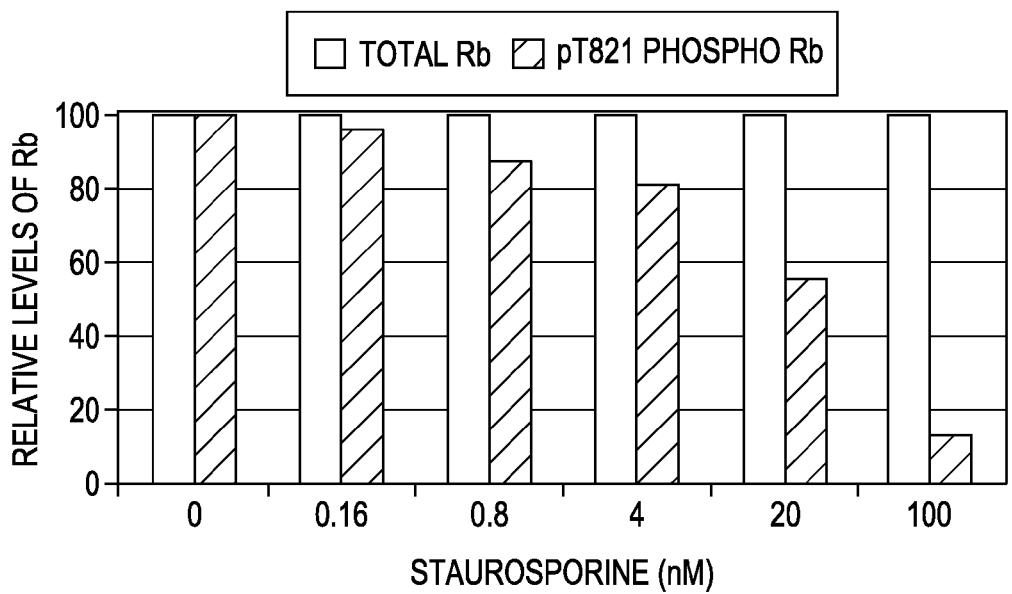
FIG. 12 shows the application of the Rb [$pT^{821}$] ELISA in evaluating kinase activity in Jurkat cells were grown in the presence of the kinase inhibitor, staurosporine.

Kinase reactions for Rb: Natural sources for Rb were obtained for these studies from exponentially growing cells. Endogenous cellular kinases provided the phosphorylation of the natural Rb protein. FIG. 12 shows the application of this ELISA to study kinase reactions. Jurkat cells were grown in the presence of the kinase inhibitor, staurosporine, at various concentrations for 36 hours prior to lysis. Lysates were normalized for total Rh content using the Total Rb ELISA (BioSource International catalog #KHO0011). Levels of Rb phosphorylation at threonine 821 were determined. These data show that staurosporine inhibits the phosphorylation of Rb at threonine 821, presumably through the inhibition of cdks.

EGFR System: This model system presents an analysis of the cell surface receptor Epidermal Growth Factor Receptor (EGFR). This protein is a large transmembrane signaling protein with multiple phosphorylation sites consisting of phospho-threonine, phospho-serine and phospho-tyrosine residues.

EGFR protein: Human EGFR protein was purified from human carcinoma A431 cells by affinity purification. The product is purchased from Sigma (St. Louis, Mo.; cat #E-2645).

Figure 13:
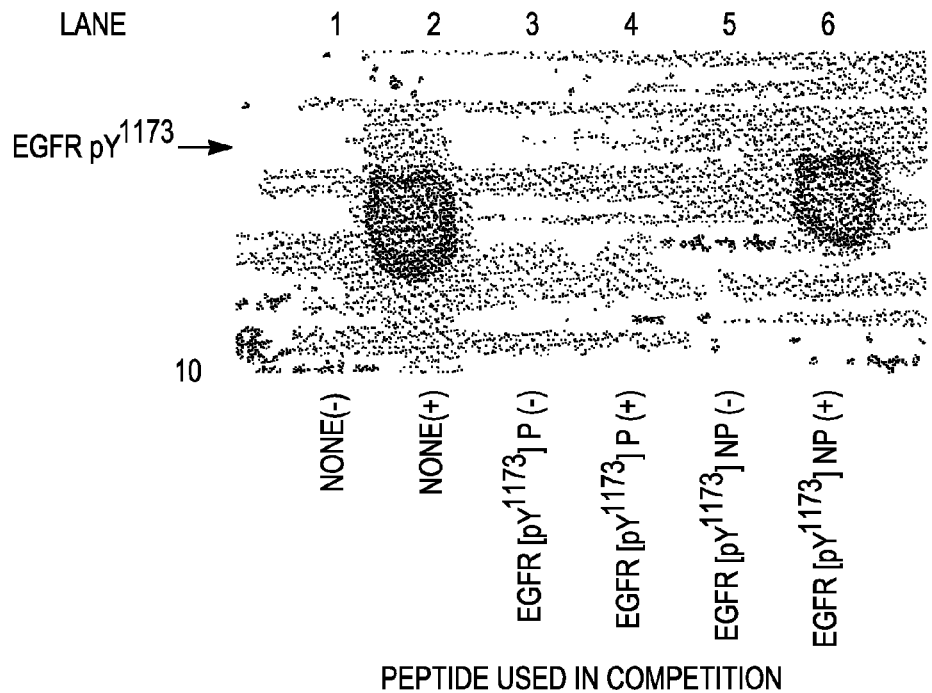
FIG. 13 illustrates the specificity of the EGFR PSSA [$pY^{1173}$].

EGFR [pY$^{1173}$]1 PSSA: Rabbit antiserum was produced against a chemically synthesized phosphopeptide derived from the region of EGFR that contains tyrosine 1173. The sequence is conserved in human, mouse, and rat. Antibody was purified from serum by sequential epitope-specific chromatography. The antibody has been negatively preadsorbed using (i) a non-phosphopeptide corresponding to the site of phosphorylation to remove antibody that is reactive with non-phosphorylated EGFR enzyme, and (ii) a generic tyrosine phosphorylated peptide to remove antibody that is reactive with phospho-tyrosine (irrespective of the sequence). The final product is generated by affinity chromatography using an EGFR derived peptide that is phosphorylated at tyrosine 1173. FIG. 13 illustrates the specificity of the EGFR PSSA [pY$^{1173}$]. Cell extracts prepared from NIH3T3 cells expressing EGFR were starved for 30 hours, then stimulated for 10 minutes with 30 ng/mL EGF (+), or left unstimulated (−), then resolved by SDS-PAGE on a 6% Tris-glycine gel, and transferred to nitrocellulose. Membranes were incubated with 0.50 µg/ml anti-EGFR [pY$^{1173}$] antibody, following prior incubation in the absence (lanes 1 & 2), or presence of the peptide immunogen (lanes 3 & 4), or the non-phosphopeptide corresponding to the EGFR phosphopeptide (lanes 5 & 6). After washing, membranes were incubated with goat F(ab')$_2$ anti-rabbit IgG alkaline phosphatase and bands were detected using the Tropix WesternStar™ detection method. The data show that only the phosphopeptide corresponding to this site blocks the antibody signal, demonstrating the specificity of the anti-EGFR [pY$^{1173}$] antibody for this phosphorylated residue.

EGFR [Py$^{845}$]1 PSSA: Prepared essentially as EGFR [pY$^{1173}$] PSSA but using chemically synthesized phosphopeptides from the region that contains tyrosine 845.

EGFR [Pan] monoclonal antibody: The capture antibody is a mouse monoclonal antibody, clone 199.12, available commercially from Neomarkers, Inc. (Union City, Calif.). It is specific for human EGFR and does not react with HER2/neu, HER3 and HER4. This antibody will bind to both non-phosphorylated and phosphorylated forms of EGFR protein and therefore is used as an initial capture antibody in the EGFR ELISA.

EGFR [Pan] Detection Antibody: This rabbit antibody was prepared by immunization with a synthetic peptide corresponding to C-terminus of human EGFR. The antibody was purified using protein A affinity column. It shows no cross-reactivity with HER2/neu, HER3 and HER4.

EGFR PSSA and Full Length ELISA: A concentration of 2.5 µg/mL of pan-EGFR monoclonal antibody in carbonate buffer, pH 9.4, was incubated at 100 µL/well in microtiter plates at 4° C. overnight. The wells were washed with a PBS/TWEEN-20 solution three times followed by blocking on other sites on the plastic surface with a buffered solution containing unrelated proteins such as BSA for 2 hours at room temperature. Autophosphorylated EGFR or non-phosphorylated EGFR were added to the wells at various concentrations and incubated for 1 hour at room temperature. After three washings with Washing Buffer, the wells were incubated, respectively, with EGFR [pY$^{845}$] PSSA, EGFR [pY$^{1173}$] PSSA, and Pan-EGFR antibodies at the optimized concentrations (ranging from 0.1 to 1 µg/mL) for 1 hour at room temperature. The plates then were washed three times with Washing Buffer, followed by the addition of an HRP conjugated anti-rabbit IgG secondary antibody at 1:2000 dilution for 1 hour at room temperature. After washing, 100 µL of Stabilized Chromogen was added to each well and then incubated for 20 minutes at room temperature in the dark. The OD values at 450 nm were measured following the addition of stop solution to each well.

Figure 14:
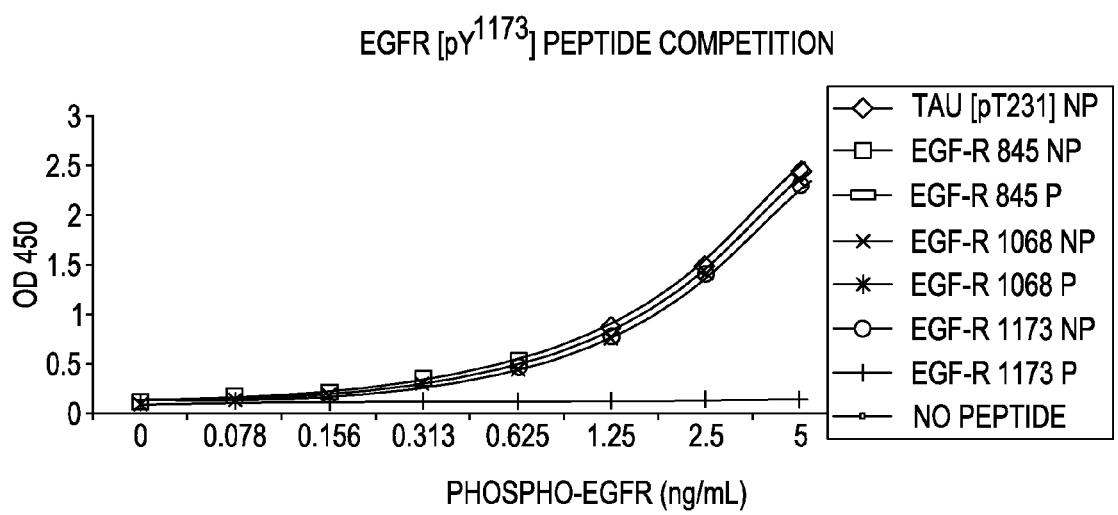
FIG. 14 shows the specificity of the EGFR [$pY^{1173}$] ELISA for tyrosine residue 1173 as determined by peptide competition.

The specificity of the EGFR [pY$^{1173}$] ELISA for tyrosine residue 1173 was determined by peptide competition. The data presented in FIG. 14 show that only the peptide corresponding to the region surrounding tyrosine residue 1173 and in the phosphorylated state could block the ELISA sipal generated with this PSSA.

Kinase Reactions: (Autophosphorylation)

EGFR was incubated to induce auto-phosphorylation in a buffer of 15 mM HEPES (pH7.4), 6 mM MnCl$_2$ and 15 mM MgCl$_2$ containing IµM ATP for 30 minutes at 30° C.

Figure 15:
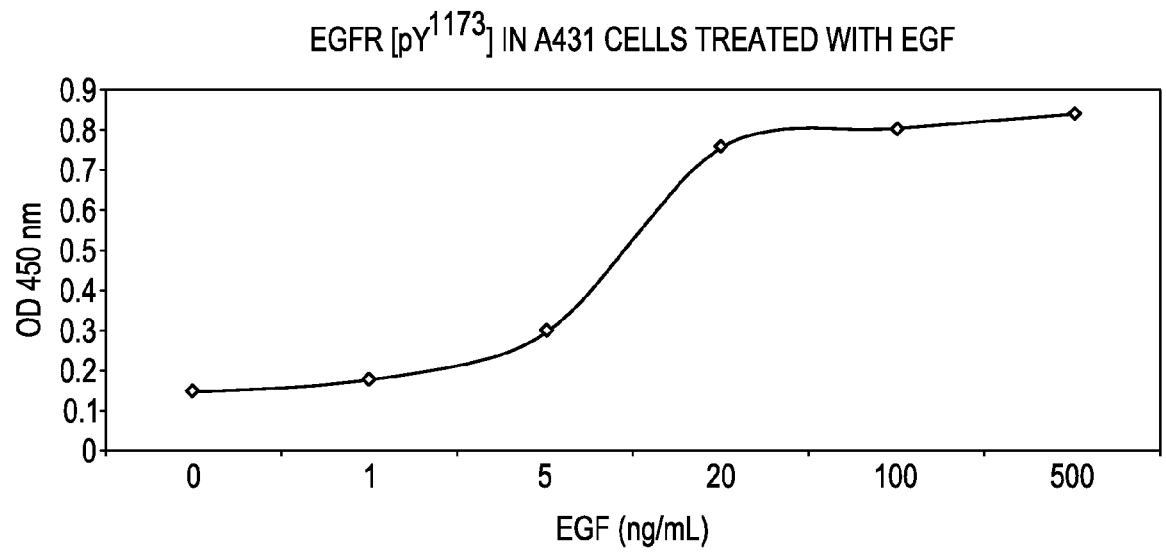
FIG. 15 demonstrates the response curve of phosphorylation of EGFR in A431 cells after treatment with EGF using the EGFR [$pY^{1173}$] ELISA.

FIG. 15 demonstrates the dose-response curve of phosphorylation of EGFR in A431 cells after treatment with EGF at 1-500 ng/mL for 10 minutes. The level of tyrosine phosphorylation of EGFR at tyrosine 1173 was detected with the EGFR [pY$^{1173}$] ELISA.

Figure 16:
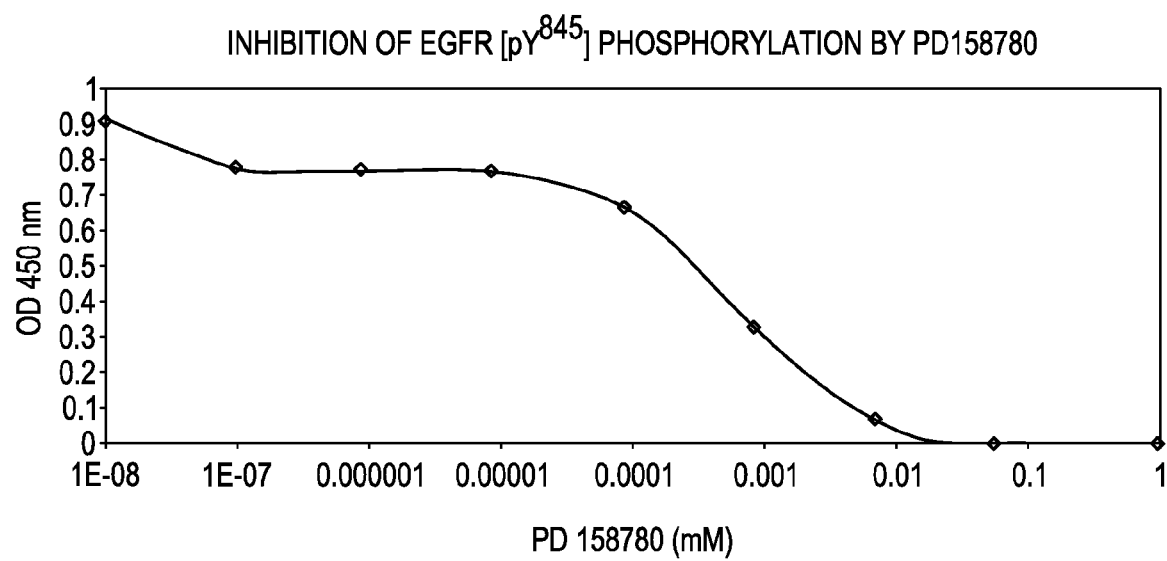
FIG. 16 shows the application of the EGFR [$pY^{845}$] ELISA in evaluating kinase activity in A431 cells were grown in the presence of the tyrosine kinase inhibitor, PDI58780.

FIG. 16 demonstrates use of the described invention to detect protein kinase activity associated with EGFR at tyrosine residue 845 and inhibition of that activity by a protein kinase inhibitor. In this assay, 2 ng/vial of purified human EGFR. was incubated (auto-phosphorylated) in the buffer of 15 mM HEPES (pH7.4), 6 mM MnCl$_2$ and 15 mM MgCl$_2$ containing 1 uM ATP for 30 minutes at 30° C. To inhibit phosphorylation of EGFR [py$^{845}$]' tyrosine kinase inhibitor PD158780 (Calbiochem, cat #. 513035) was added to the reaction at the indicated concentration (see FIG. 16). EGFR [pY$^{845}$] phosphorylation was measured using 4 ng/mL of EGFR and the EGFR [pY$^{845}$] PSSA ELISA.

Table 1: Partial List of signal transduction proteins for which site-specific phosphorylation can be determined by methods of the present invention.

TABLE 1

Examples of Signal Transduction Proteins
Protein

A alpha-actinin
alpha-synuclein
ABL/c-Abl (Abelson nonreceptor protein tyrosine kinase)
Acetylcholine Receptor
Ack nonreceptor protein tyrosine kinase;
Ak1JPKB serine/threonine protein kinase
AP-1 (Activator protein-1 jur/fos dirneric transcription factors
AP-2 (Activator protein-2 transcription factor

TABLE 1-continued

Examples of Signal Transduction Proteins
Protein

Apaf-I (Apoptosis protease-activating factor-1)
Apaf-2 (Apoptosis protease-activating factor-2/cytochrome C)
Apaf-3 (Apoptosis protease-activating factor-3/caspase-9
Arp2/3 (Actin related protein)
Atf-1 (Activating transcription factor-1)
Atf-2 (Activating transcription factor-2)
Atf-3 (Activating transcription factor-3)
Atf-4 (Activating transcription factor-4)
ATM (Ataxia Telangiectasia Mutated. Protein)

B

B-ATF nuclear basic leucine zipper protein/transcription factors
Bad
Bak
Bax
Bcl-2 (B-cell chronic lymphocytic leukemia 2)
Bcl-xL
Bcl-xS
BCR/ABL protein tyrosine kinase
beta-Catenin
BID (BH-3 Interacting Death Domain)
Blk (B Lymphocyte Src non-receptor protein tyrosine kinase family member)
BMK-1 (Big Map Kinase/ERK5)
Btk (Bruton's Tyrosine Kinase)

C

Cadherin
CADTK (calcium activated protein tyrosine kinase/Cakbetalpyk2/FAK2fRAFTK) CAK (Cdk-Activating Kinase)
Cak-beta (Cell adhesion kinase beta/CADTK/Pyk2/FAK2/RAFTK)
caldesmon
calmodulin
calpain cysteine proteases
CaM kinase 11 (Calmodulin-dependent protein kinase II)
CB 1 (Cannabinoid Receptor 1)
CB2 (Cannabinoid Receptor 2)
caspase-2 (Cysteine Aspartyl Protease-2/ICH-1/NEDD-2)
caspase-3 (Cysteine Aspartyl Protcase-3/LICE/CPP32/YAMA/apopain/SCA-1)
caspase-8 (Cysteine Aspartyl Protease-8/MACH/FLICE/Mch5)
caspase-9 (Cysteine Aspartyl Protease-9/1CE-LAP6/Mch6/APAF-3)
Caveolin 1, 2, and 3)
CD45 transmembrane tyrosine phosphatase
CD45AP (CD45-associated protein)
c-fos transcription factor
CDK1/cdc2 (Cyclin-dependent kinase-1)
CDK2 (Cyclin dependent kinase-2)
CDK4 (Cyclin dependent kinase-4)
CDK5 (Cyclin dependent kinase-5)
c-Jun transcription factor
c-myc transcription factor
Cortactin
COX-2 (Cyclooxygenasc-2/prostaglandin-endoperoxide synthase-2)
c-kit receptor protein
c-raf protein serine/threonine kinase
CREB transcription factor
Crk SH2 and SH3 domain-containing adaptor protein
CSK (Carboxyl-terminal Src Kinase)
cytochrome-c

D

DAPK (Death Associated Protein Kinase)
desmin
DNA-PK (DNA dependent protein kinase)

E

E2F-1 DNA binding protein
EGF-R (Epidermal Growth Factor Receptor)
eIF-2alpha (Eukaryotic translation Initiation Factor 2alpha)
ERK1/MAPK (Extracellular signal-Regulated/Nlitogen-Activated Protein Kinase 1)
ERIK2/MAPK (Extracellular signal-RegulatedMitogen-Activated Protein Kinase 2)
ERK3 (Extracellular signal-Regulated/p62 Mitogen-Activated Protein Kinase 3)

TABLE 1-continued

Examples of Signal Transduction Proteins
Protein

ERK4 (Extracellular signal-Regulated Protein Kinase 4)
ERK5 (Extracellular signal-Regulated Protein Kinase 5/Big MAP Kinase 1)
ERK6 (Extracellular signal-Regulated Protein Kinase 6/p38garruna)
ERK7 (Extracellular siznal-Regulated Protein Kinase 7)
ERK5 (Extracellular signal-Regulated Protein Kinase 8)

F

F-actin
FADD (Fas-associated Death Domain)
FAK (Focal Adhesion Kinase/pp125FAK)
FAS (FAS-Ligand Receptor)
F C, non-receptor Src family tyrosine kinase
Fos B
Fra-1 (Fos-related antigen-1)
Fra-2 (Fos-related Antigen-2)
FRK (Fos-Regulating Kinase)
FYB (Fyn binding protein)
Fyn non-receptor Src family tyrosine kinase

G

Gab 1 (Grb2-associated binder 1)
Gab 2 (Grb2-associated binder 2)
GCK (Germinal Center Kinase)
GEF (Guanine nucleotide Exchange Factor)
Giα inhibitory guanine nucleotide regulatory protein
Giβ inhibitory guanine nucleotide regulatory protein
Giγ inhibitory guanine nucleotide regulatory protein
Gq/11 guanine nucleotide-binding protein
Gq/11β guanine nucleotide-binding protein
Gq/11γ guanine nucleotide-binding protein
Grb2 (Growth factor Receptor Binding protein-2)
Grk2 (G protein-coupled Receptor Kinase)
GSK-3α (Glycogen Synthase Kinase 3alpha)
GSK-3β (Glycogen Synthase Kinase 3beta)

H

Hck (Hematopoietic cell kinase)
HGF-R (Hepatocyte growth factor receptor)
Hrk (3-Hydroxy-3-methyl glutaryl-coenzyme A Reductase Kinase)

I

IkappaB alpha NFkB inhibitory protein
IkappaB beta NFkB inhibitory protein
IKKalpha (IkB kinase alpha)
IKKbeta (IkB kinase beta)
IKKgamma (IkB kinase gamma/NEMO)
1GF-I receptor (Insulin-like growth factor-I receptor)
Insulin receptor
Integrins
Integrin-Associated Protein (IAP/CD47)
IRAK (Interleukin-1 Receptor-Associated Kinase)
IRK (Insulin Receptor Kinase)
IRS-1 (Insulin Receptor Substrate 1) IRS-2 (Insulin Receptor Substrate 2)

J

JABI (Jun-Activation domain Binding protein I)
SAKI (Janus Activating Kinase 1)
JAK2 (Janus Activating Kinase 2)
JAK3 (Janus Activating Kinase 3)
JNK1/SAPKγ (c-Jun amino-terminal kinase I/Stress-Activated Protein Kinase y)
INK2/SAPKβ (c-Jun amino-terminal kinase 2/Stress-Activated Protein Kinase 13)
JNK3/SAPKα (c-Jun amino-terminal kinase 3/Stress-Activated Protein Kinase a)

L

LAST (Linker for Activation of T cells)
Lck non-receptor Src family protein tyrosine kinase
Lyn non-receptor Src family protein tyrosine kinase

M

MEF2c transcription factor
MEKI (Mitogen-activated ERK-activating Kinase 1)

TABLE 1-continued

Examples of Signal Transduction Proteins
Protein

MEK2 (Mitogen-activated ERK-activating Kinase 2)
MEK3 (Mitogen-activated ERK-activating Kinase 3)
MEK4 (Mitogen-activated ERK-activating Kinase 4)
MEK5 (Mitogen-activated ERK-activating Kinase 5)
MEKKI (MEK kinase 1)
Met (c-metEGF-receptor)
MKP 1 (MAP Kinase Phosphatase 1)
MKP 2 (MAP Kinase Phosphatase 2)
MKP 3 (MAP Kinase Phosphatase 3)
MKP 4 (MAP Kinase Phosphatase 4)
MKP 5 (MAP Kinase Phosphatase 5)
MKP 6 (MAP Kinase Phosphatase 6)
MLCK (Myosin light chain kinase)
MuSK (Muscle specific serine/threonine kinase)
Myosin
MLCK PPase (Myosin Light Chain Kinase Phosphatase)

N

Beta-NAP (Beta-Neuron Adaptor Protein/AP-3)
NATI/DAP-5 (Novel APOBEC-1 Target no. 1/Death-Associated Protein-5)
NCK SH2 and SH3 domains-containing transforming protein
Nek2 (Nima-related Kinase2)
NFAT-1 (Nuclear Factor of Activated T-cells)
NfkappaB (Nuclear Factor Kappa B transcription factor)
NIK (NFkappaB Inducing Kinase)
NTK (Nervous Tissue and T cell Kinase)

P p130cas
p190Rho GAP GTPase
P2Y2 purinoceptor
p36 CAK assembly/activation factor
p38 (ERK6 MAPK/SAPK)
p38d (SAPK4)
p53 Tumor suppressor gene.
p58 IPK (Inhibitor of the interferon-induced double-stranded RNA-activated Protein Kinase, PKR)
p62dok GAP-associated protein
p62 lck ligand/ZIP
p68 kinase
p96
PAK1 (p21-Activated protein Kinase 1)
PAK2 (p21-Activated protein Kinase 2)
PAK3 (p21-Activated protein Kinase 3)
PARP (Poly(ADP-Ribose) Polyrncrase)
Paxillin
PCNA (Proliferating Cell Nuclear Antigen)
PDGF Receptor (Platelet Derived Growth Factor Receptor)
PDK1 (Phosphoinositide-Dependent Kinase-1)
PDK-2 (Phosphoinositide-Dependent Kinase-2/Integrin-linked kinase)
PECAM-1 (Platelet-Endothelial Cell Adhesion Molecule-1)
P13K (Phosphatidyl Inosito 1-3-Kinase)
PIAS (Protein Inhibitors of Activated STATs)
PITP alpha (Phosphatidylinositol Transfer Protein alpha)
PKA alpha/cAMP-dependent protein kinase
PKB (Protein kinase B)
PKC alpha (Protein Kinase C alpha)
PKC beta (Protein Kinase C beta)
PKC delta (Protein Kinase C delta)
PKC gamma (Protein Kinase C gamma)
PKD (Protein Kinase D)
PKR (Protein Kinase R or double-stranded RNA-activated protein kinase)
PLC-gamma 1 (Phospholipase C-gamma 1)
PRK (Proliferation Related Kinase)
PTEN (MMAC1 tumor suppressor gene/protein phosphatase)
Pyk2 (CAKbeta/FAK2/RAFTK) Protein tyrosine Kinase

R

Rac/cdc42 GTPase
Rafl (C-raf) serineithreonine protein kinase
A-Raf serine/threonine protein kinase
B-raf serine/threonine kinase
V-Raf viral serine/threonine protein kinase
RAFTK (Related Adhesion Focal Tyrosine Kinase)

TABLE 1-continued

Examples of Signal Transduction Proteins
Protein

RAIDD (RIP-Associated ICH-1/CED-3 homologous protein with a Death Domain)
Rapt GTPase
Rap 1-GAP (C3G) inactivator of Rap-1
Rapsyn
Ras GTPase
Rb (Retinoblastoma tumor suppressor protein)
Rho Small molecular weight GTPase
RIP (Receptor Interacting Protein)
ROCK (Rho-activated kinase)

S

S6k (S6 Kinase)
Shc
SHIP (SH2 domain containing inositol phosphatase)
SH-PTPI Protein Tyrosine Phosphatase
SH-PTP2 Protein Tyrosine Phosphatase
SIRPalpha1 (Signal Related Protein Alpha)
SIP1 (Smad Interacting Protein 1)
Smad2 (Sma and Mad-related 2)
Smad3 (Sma and Mad-related 3
Smad5 (Sma and Mad-related 5)
Smad7 (Sma and Mad-related 7)
SOCS-1 (Suppressor of Cytokine Signaling-1)
SOCS-2 (Suppressor of Cytokine Signaling-2)
SOCS-3 (Suppressor of Cytokine Signaling-3)
SOS (Son of Sevenless)
Src non-receptor tyrosine kinase
SRF (Serum Response Factor)
SRPK1 (SR protein-specific Kinase 1)
SRPK2 (SR protein-specific Kinase2)
STAT1alpha (Signal Transducer and Activator of Transcription 1)
STAT2 (Signal Transducer and Activator of Transcription 2)
STAT3 (Signal Transducer and Activator of Transcription 3)
STAT4 (Signal Transducer and Activator of Transcription 4)
STAT5alpha (Signal Transducer and Activator of Transcription 5alpha)
STAT5beta (Signal Transducer and Activator of Transcription 5 beta)
STAT6 (Signal Transducer and Activator of Transcription 6)
Syk (Spleen tyrosine kinase)
Syndecans transmembrane proteoglycan

T

Takl (TGF-bl activated kinase)
Talin
TANKII-TRAF (TNT Receptor Activating Factor)
Tau mierotubule-associated protein
TBK-liT2K (TANK Binding Kinase 1)
Tensin
TNF-RI (Tumor Necrosis Factor Receptor I)
TRADD (TNT-Receptor Associated Death Domain protein)
TRAF1 (TNF-Receptor Associated Factor 1)
TRAF2 (TNF-Receptor Associated Factor 2)
TRAF3 (TNF-Receptor Associated Factor 3)
TRAF4 (TNF-Receptor Associated Factor 4)
TRAF5 (TNF-Receptor Associated Factor 5)
TRAF6 (TNF-Receptor Associated Factor 6)
TrkA protein tyrosine receptor kinase A
TrkB protein tyrosine receptor kinase B
TrkC protein tyrosine receptor kinase C

V

VEGF-receptor (vascular endothelial growth factor receptor, types 1. 2, 3)
Vinculin

W

WASP (Wiskott-Aldrich Syndrome Protein)

Z

ZIP (Zeta Interacting Protein)
ZIP kinase (zipper serine/hreonine kinase)
ZRP-1 (Zyxin Related Protein)
Zyxin The examples provided illustrate the present invention and are not intended to limit the invention in spirit or scope.

Similarly, the description of these reagents and methods can be used in an inverse function to analyze the activity of protein specific phosphatases, enzymes that remove phosphate groups from specific amino acid residues. In addition, Antibodies of the present invention are also useful for inactivating phosphorylated polypeptides for therapeutic purposes.

What is claimed is:

1. A method for quantitatively measuring kinase activity of a kinase comprising:
    (a) contacting a protein with the kinase to phosphorylate a phosphorylation site on the protein;
    (b) capturing the protein with a first pan antibody that binds both a phosphorylated and non-phosphorylated form of the protein to form a captured protein;
    (c) contacting the captured protein with a phosphorylation site-specific antibody (PSSA) wherein the PSSA binds to the phosphorylated phosphorylation site on the protein to form a bound phosphorylated protein;
    (d) contacting the captured protein with a second pan antibody that binds both the phosphorylated and non-phosphorylated form of the protein, wherein the second pan antibody recognizes an epitope on the protein that is not recognized by the first pan antibody to form a bound total captured protein;
    (e) detecting the PSSA bound to the phosphorylated protein; and
    (f) detecting the second pan antibody bound to the total captured protein, to determine the fraction of the protein that is phosphorylated at the phosphorylation site, thereby quantitatively measuring the kinase activity of the kinase.

2. The method according to claim 1, wherein the kinase is selected from the group consisting of glycogen synthetase kinase 3 beta (GSK-3β), cAMP-dependent protein kinase (PKA), protein kinase C (PKC), cyclin dependent kinase 5 (CDK-5), microtubule affinity regulating kinase (MARK), c-Jun amino terminal kinase (JNK), p38 mitogen activated protein (p38MAPK), and casein kinase II.

3. The method according to claim 1, wherein the protein is Tau protein, epidermal growth factor receptor (EGFR) protein, or retinoblastoma (Rb) protein.

4. The method according to claim 3, wherein the phosphorylation site of the Tau protein is $T^{39}$, $T^{181}$, $S^{184}$, $S^{195}$, $S^{198}$, $S^{199}$, $S^{202}$, $T^{205}$, $T^{212}$, $S^{214}$, $T^{217}$, $T^{231}$, $S^{235}$, $S^{262}$, $S^{320}$, $S^{324}$, $S^{356}$, $S^{361}$, $S^{396}$, $S^{400}$, $T^{403}$, $S^{404}$, $S^{409}$, $S^{412}$, $S^{413}$, $S^{416}$, or $S^{422}$.

5. The method according to claim 3, wherein the phosphorylation site of the EGFR protein is $Y^{845}$, $Y^{992}$, $Y^{1068}$, $Y^{1086}$, or or $Y^{1173}$.

6. The method according to claim 3, wherein the phosphorylation site of the Rb protein is $T^{821}$, $T^{356}$, $S^{807/811}$, $S^{249}/T^{252}$ or $S^{751}$.

7. The method according to claim 1, wherein the protein is a signal transduction protein, a cell surface receptor, a cell cycle regulation protein, a nuclear protein, or a cytoplasmic protein.

8. The method according to claim 1, wherein the protein is a full length protein.

9. The method according to claim 1, wherein the protein is a recombinant protein.

10. The method according to claim 1, wherein the PSSA and the second pan antibody are rabbit antibodies and the first pan antibody is a mouse antibody.

11. The method according to claim 1, wherein the first pan antibody is a mouse monoclonal antibody and the second pan antibody is a polyclonal antibody.

12. The method according to claim 1, wherein the first pan antibody is a monoclonal antibody.

13. The method according to claim 1, wherein the PSSA is a polyclonal antibody.

14. The method according to claim 1, wherein the method is performed in a microtiter plate.

15. The method according to claim 14, wherein the contacting with the PSSA is performed in a first microtiter plate well and the contacting with the second pan antibody is performed in a second microtiter plate well.

16. The method according to claim 1, wherein contacting the protein with the kinase is performed by incubating the protein with various concentrations of the kinase.

17. The method according to claim 1, wherein the method is a high-throughput method.

18. The method according to claim 1, wherein contacting the protein with the kinase is performed in the presence of a potential drug to interfere with kinase activity.

19. A kit for the measurement of kinase activity on a protein comprising:
(a) a first pan antibody specific for and that binds both a phosphorylated and non-phosphorylated form of the protein;
(b) a second pan antibody that binds to an independent site on the protein from the first pan antibody; and
(c) a phosphorylation site-specific antibody (PSSA) wherein the PSSA binds to a target phosphorylation site on the protein only when the target phosphorylation site on the protein is phosphorylated.

20. The kit according to claim 19, which further comprises a buffer.

21. The kit according to claim 19, which further comprises non-phosphorylated and phosphorylated protein standards.

* * * * *

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: chemically synthesized phosphopeptide
<220> FEATURE:
<221> NAME/KEY: PHOSPHORYLATION
<222> LOCATION: 6

<400> SEQUENCE: 1

Arg Ser Gly Tyr Ser Ser Pro Gly Ser Pro Gly
1               5                   10

<210> SEQ ID NO 2
<211> LENGTH: 13
<212> TYPE: PRT
<213> ORGANISM: Artificial Sequence
<220> FEATURE:
<223> OTHER INFORMATION: chemically synthesized phosphopeptide
<220> FEATURE:
<221> NAME/KEY: PHOSPHORYLATION
<222> LOCATION: 8

<400> SEQUENCE: 2

Gly Ser Arg Ser Arg Thr Pro Ser Leu Pro Thr Pro Pro
1               5                   10
```